United States Patent [19]

Stalling et al.

[11] Patent Number: 5,281,406
[45] Date of Patent: Jan. 25, 1994

[54] RECOVERY OF $C_{60}$ AND $C_{70}$ BUCKMINSTERFULLERENES FROM CARBON SOOT BY SUPERCRITICAL FLUID EXTRACTION AND THEIR SEPARATION BY ADSORPTION CHROMATOGRAPHY

[75] Inventors: David L. Stalling; Said Saim; Congyuan Guo; Kenneth Kuo, all of Columbia, Mo.

[73] Assignee: Analytical Bio-Chemistry Laboratories, Inc., Columbia, Mo.

[21] Appl. No.: 874,473

[22] Filed: Apr. 22, 1992

[51] Int. Cl.$^5$ .................... C01B 31/00; C01B 31/02
[52] U.S. Cl. .................... 423/445 B; 423/461
[58] Field of Search .................... 423/445 B, 461; 210/635; 436/52

[56] References Cited

U.S. PATENT DOCUMENTS 4,983,528 1/1991 Loucks .................... 210/656

OTHER PUBLICATIONS

Meier et al. *Journal of Organic Chemistry*, vol. 57, No. 6, Mar. 13, 1992, pp. 1924–1926.
Kikuchi et al. *Chemical Physics Letters*, vol. 188, No. 3,4, Jan. 10, 1992, pp. 177–180.
Kikuchi et al, *Chemistry Letters*, No. 9, Sep. 1991, pp. 1607–1610.
Jinno et al, *Journal of Chromatography* vol. 594, No. 1&2, Mar. 6, 1992, pp. 105–109.
Pirkle et al., *Journal of Organic Chemistry*, vol. 56, No. 25, Dec. 6, 1991 pp. 6973–6974.
Ajie et al, *Journal of Physical Chemistry*, vol. 94, No. 24, 1990, pp. 8630–8633.
Cox et al., *Journ. of American Chemical Society*, vol. 113, No. 8, Apr. 10, 1991, pp. 2940–2944.
Vasallo et al, *Journ. of Chemical Society, Chemical Communications*, No. 1, Jan. 1, 1992 pp. 60–61.

*Primary Examiner*—Michael Lewis
*Assistant Examiner*—Stephen G. Kalinchak

[57] ABSTRACT

A process has been developed to effectively separate and recover essentially pure amounts of both $C_{60}$ and $C_{70}$ from carbon soot and higher molecular weight fullerenes. This process first extracts the fullerenes from carbon soot and then sequentially separates the $C_{60}$ and $C_{70}$ molecules using high performance or low pressure adsorption chromatography packed column containing a gel polymer having aromaticity and a pore size ranging from 10 to 500 Å.

In this process, a first stage of fractionation of the fullerenes is preferably accomplished by selective supercritical fluid extraction (SFE) of $C_{60}$. Unrecovered $C_{60}$ and $C_{70}$ molecules are then extracted by supercritical fluid extraction at a higher pressure and/or higher temperature.

23 Claims, 17 Drawing Sheets

RECOVERY OF $C_{60}$ AND $C_{70}$ BUCKMINSTERFULLERENES FROM CARBON SOOT BY SUPERCRITICAL FLUID EXTRACTION AND THEIR SEPARATION BY ADSORPTION CHROMATOGRAPHY

BACKGROUND OF THE INVENTION

Although the existence of a round, hollow, geodesic-sphere shaped molecule consisting of 60 carbon atoms was first proposed in 1985 by Kroto et al. (*Nature*, Vol. 318, p. 162, 1985), it was not until 1990 that measurable amounts of this substance were prepared by Krätschmer et al. (*Nature*, Vol. 347, p. 354, 1990). This molecule was later named buckminsterfullerene or fullerene in honor of Buckminster Fuller, the inventor of the geodesic dome.

This form of carbon was obtained by resistive heating of graphite rods in an inert helium atmosphere. It is now known that fullerenes may be produced even from coal (Dance et al. *J. Phys. Chem.*, 95, p. 8425, 1991), a cheaper alternative to the graphite process. It has also been determined that, besides the normally occurring carbon soot contaminants such as benzene, anthracene and other polynuclear aromatics, a variety of other different carbon complexes exist, including less round, yet hollow, molecules such as $C_{32}$, $C_{50}$, $C_{70}$, $C_{84}$, and other fullerenes even larger than $C_{960}$. This new form of carbon complements the well known pyramidal shape of diamond carbon, and the hexagonal shape of graphite sheets.

The reported stability and reactivity of these complexes opens broad avenues for new applications and products such as superconductors, high-temperature lubricants and catalysts. $C_{60}$ is reported to be stable to pressures up to $2.5 \times 10^6$ psi (Yoo and Nellis, *Science*, 254, p. 1489, 1991) and, like carbon graphite is stable in many organic solvents for several weeks. High resonance energy of $C_{60}$ and $C_{70}$ brought about by their conjugated double bonds is responsible for their enhanced molecular stability and strength.

Simple resistive heating yields less fullerenes than vaporization by plasma arc or Nd:YAG laser vaporization. In the plasma arc method, the two rods are brought to touch each other to strike an arc and then are separated to a distance where maximum plasma brightness occurs. Using this method, yields of soluble material, mainly fullerenes $C_{60}$–$C_{266}$, of up to 44% are obtainable.

Mixtures of fullerene complexes in carbon soot as prepared by a contact arc method are available from MER Corporation of Tucson, Arizona. By far the most abundant of all fullerenes in the raw soot are $C_{60}$ and $C_{70}$, with a ratio $C_{60}/C_{70}$ of about 7/1. However, fractional content of these compounds in the carbon soot obtained by this method can vary widely, between approximately three (3) and 33 percent by weight. It is thus highly desirable to find a separation technique that provides substantially pure fractions of $C_{60}$ and $C_{70}$ in order to expand the use of such compounds.

Conventionally, solutes in solid matrices are recovered by either liquid extraction or sublimation. Liquid extraction generally consists of exposing a quantity of the solid matrix to a liquid solvent for a period long enough to transfer most soluble material into the liquid phase. Solvents such as hexane, benzene, and toluene are currently used for extraction. Selective extraction of $C_{60}$ and $C_{70}$ from the soot is typically obtained by extraction with hexane.

Extraction of fullerenes by sublimation essentially involves evaporation of the volatile material under vacuum and/or in an inert atmosphere into a gas phase maintained at a temperature above the sublimation temperature of the desired fullerenes (400°–600° C. for $C_{60}$). The fullerenes are then recovered in nearly pure form on separate regions of a cooled collector.

While liquid extraction is most efficient at recovering the bulk of the extract, it is non-selective, time consuming, and generally requires further cleanup and fractionation of the extract.

Another extraction method known in the art is supercritical fluid extraction (SFE). SFE makes use of supercritical fluids (SCFs) as extraction solvents, i.e. fluids at temperatures and pressures above their critical temperature and critical pressure. SCFs are neither gaseous nor liquid, but rather exhibit intermediate properties between gas and liquid properties. However, while SCF densities, i.e. solvent power, are comparable to liquid densities, SCF transport properties such as viscosity and diffusivity are essentially halfway between gas and liquid properties. As a consequence of the combined high solvent power and high diffusivity of SCFs, SFE is relatively rapid, selective, and efficient, and its operating conditions of temperature, pressure, and nature of extraction solvent can be adjusted to quantitatively extract a variety of analytes from solid or liquid matrices. Furthermore, when appropriate, SFE can be conducted with $CO_2$ as a SCF. Besides its mild critical temperature and pressure ($T_c=31°$ C., $P_c=1070$ psi), $CO_2$ is non-toxic, inexpensive and easily removed from the extract by pressure reduction. However, while $CO_2$ is the most widely used SFE solvent, its lack of polarity and aromaticity limit its utility as SFE solvent to small or relatively non-polar and hydrophobic molecules, and is thereby not expected to recover quantitative amounts of fullerenes.

Following extraction by either method, pure $C_{60}$ and $C_{70}$ are obtained by separation from other extracted material. Separation of $C_{60}$ from low molecular weight compounds and higher fullerene extracts on an alumina column was reported by Diedrich et al. (*Science*, in print). In this method, the extract is first adsorbed on neutral alumina, and then chromatographed on the same alumina column with a mixture of 5% hexane in toluene to elute $C_{60}$, and 10–50% hexane in toluene to elute $C_{70}$. In the same manner, $C_{60}$ can be separated from a fullerene mixture on a graphite column (Vassalo et al., *J. Chem. Soc. Chem. Commun.*, p. 60, 1992), but recovery of $C_{70}$ and higher fullerenes is done by soxhlet.

SUMMARY OF THE INVENTION

A process has been developed to effectively separate and recover essentially pure amounts of both $C_{60}$ and $C_{70}$ from the lighter contaminants and heavier fullerenes present in the carbon soot. In this process, a first stage of fractionation of the fullerenes may be accomplished by selective extraction of $C_{60}$ at moderate supercritical conditions. Unrecovered $C_{60}$ and $C_{70}$ molecules are optionally further extracted by SFE at a higher pressure and/or higher temperature. $C_{60}$ and $C_{70}$ are then individually separated from the lower and higher molecular weight extract components by adsorption chromatography, preferably using high performance Envirosep-ABC columns packed with a polystyrene divinylbenzene (PSDVB) gel polymer having aromaticity and exhibiting a mean pore size ranging from 10 to 500 Å. Reaction products of surface modified $C_{60}$ and $C_{70}$ are also separable using the same columns.

DETAILED DESCRIPTION OF THE INVENTION

Figure 1:
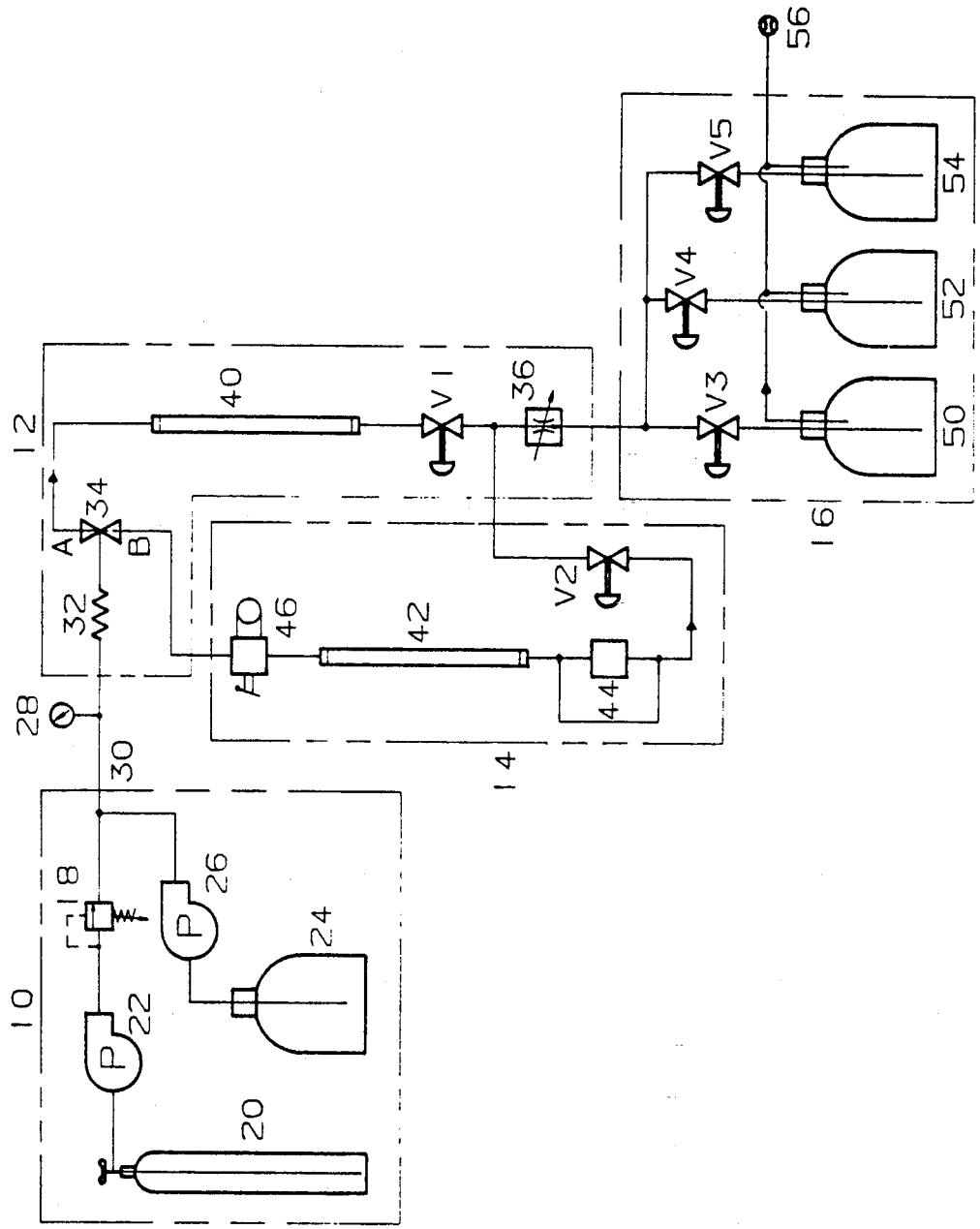
FIG. 1 is an explanatory and simplified view of an embodiment of an extraction and separation apparatus making use of SCFs and liquid solvents and mobile phases according to the present invention.

This invention relates to a process for the separation and recovery of two species of fullerenes from carbon soot. In this disclosure a mixture of fullerenes, hereinafter identified as fullerenes, includes substituted and unsubstituted $C_{60}$, $C_{70}$, and other higher and lower molecular weight fullerenes. According to the present invention, substituted and unsubstituted $C_{60}$ and $C_{70}$ fullerenes can be individually separated and recovered from a mixture of fullerenes in carbon soot in a rapid and convenient manner by utilizing SFE and adsorption chromatography, also referred to as high performance liquid chromatography (HPLC).

As previously discussed, the fullerene samples as prepared by a contact arc method are supplied in admixture with carbon soot. The process of the present invention utilizes SFE to extract the fullerenes from the carbon soot and then passes the extracted fullerenes into a preparative chromatography column to sequentially separate the $C_{60}$ and $C_{70}$ species of fullerenes for recovery. The extraction step can optionally be conducted with a liquid solvent at a temperature and pressure such that the solvent is either in a saturated state (pressure=saturation pressure), or a condensed state (pressure>saturation pressure). Suitable liquid solvents include hexane, heptane, tetrahydrofuran, methylene chloride (or dichloromethane), benzene, toluene, carbon tetrachloride, mixtures of toluene/ethyl acetate, or methylene chloride/cyclohexane and the like.

Increased selectivity towards a given fullerene of interest can be achieved by extraction at supercritical conditions wherein the mobile phase for SFE is a SCF such as $CO_2$, preferably in admixture with a solvent modifier such as the above-identified solvents, preferably toluene or methylene chloride. Both modifier concentration as well as temperature and pressure may be used to adjust solvent power and selectivity of the SCF mixture. The ability of SCF solvents to fractionate the extractable material of the carbon soot by pressure and/or temperature tuning of the solvent power appears to be possible due to the relatively large difference in molecular weight and size of the fullerenes, which yields different threshold solubility densities. Selection of the SCF and the operating conditions should provide a powerful means for selectively extracting any desired fullerenes.

By definition, a fluid is said to be supercritical if its temperature and pressure exceed its critical temperature and critical pressure respectively. Such a fluid cannot be liquified upon any further increase in pressure. A SCF exhibits gas-like mass transfer and liquid-like solvating characteristics. Hence, enhanced solute (i.e. $C_{60}$ and $C_{70}$) diffusion through the carbon soot and the SCF phase and correspondingly improved extraction rates are obtained with little compromise on solvent power. Organic modifiers are added in low concentrations ($<20\%$) to non-polar SCFs such as $CO_2$ to either aid in extraction of relatively polar sample materials, or to extract specific materials that have a high affinity for the modifier. Because of the inadequate solvent power of supercritical $CO_2$, small amounts of organic solvent modifier must be added to $CO_2$ so that the fullerenes, i.e. $C_{60}$, $C_{70}$ and related fullerene molecules, have sufficient solubility in the solvent to make the present method efficient as a separation and purification process, while keeping organic solvent modifier consumption minimal. Suitable organic modifiers for use in the extraction solvent phase include toluene, methylene chloride, and any solvent having sufficient solvent power to dissolve the fullerenes while the insoluble carbon soot remains unaffected.

It is highly desirable to utilize the same mobile phase for extraction and chromatographic separation. In order to reduce consumption and disposal costs of organic solvents, it is preferable to utilize a SCF in both the extraction as well as the chromatographic separation steps of the process.

The use of a SCF for both the extraction and chromatographic separation steps of the process eliminates the need to evaporate large quantities of organic solvent in order to concentrate or recover the separated components. Also, use of $CO_2$ as a SCF mobile phase minimizes hazardous waste solvent to be either reclaimed or disposed of. Other suitable SCFs for use in the present process include but are not restricted to: Freon 22 ($CHClF_2$), nitrous oxide, methylene chloride, methanol, ammonia, ethanol, methane, propane, ethane, ethylene, toluene or hexafluorosulfur ($SF_6$).

A further preferred embodiment of the present invention will be explained hereinunder with reference to the accompanying drawings, but it is to be understood that the present invention is not restricted to t is embodiment.

FIG. 1 shows the structure of a preferred embodiment of an extraction and separation apparatus using one SFE column and one separation column. Another preferred process for extraction and recovery of fullerene species from carbon soot can be performed using the apparatus described in a copending U.S. application Ser. No. 07/727,464 entitled "Integrated Instrument for Supercritical Fluid Sample Extraction, Sample Separation and Concentration", by David L. Stalling and Said Saim, filed on Jul. 9, 1991, which is herein incorporated by reference.

While $CO_2$ is demonstrated as the SCF, it is understood that other SCFs and SCF mixtures can be utilized in the extraction stage, and other organic solvents can be used as chromatography mobile phases. Moreover, on-line SFE-chromatography, as described in the above referenced copending U.S. application, wherein the extract is deposited directly into a column and subsequently fractionated by chromatography is also included as an embodiment of this invention.

The extraction and separation apparatus shown in FIG. 1 includes a fluid supply section 10, an extraction section 12, a separation section 14, and a sample collection section 16.

The feed supply section 10 includes a SCF supply cylinder 20, a pump 22 connected to the outlet of the cylinder 20, a solvent modifier (or chromatography mobile phase) tank 24, a pump 26 connected to the outlet of the tank 24, and a back pressure regulator 18.

The extraction section 12 includes a heat exchanger 32, a 3-port, 2-position switching valve 34, an extraction column 40, a metering valve 36, and on/off valve V1.

The sample separation section 14 includes the sample injection or introduction valve 46, chromatography column 42, detector 44 and on/off valve V2.

The sample collection section 16 includes collection vessels 50, 52 and 54, and valves V3, V4 and V5.

The process starts by first preloading the extraction column 40 with the carbon soot in either its raw form or in its raw form premixed with diatomaceous earth or similar material to provide a firm support carrier for the fluffy carbon soot. "Chem-Tube Hydromatrix" hereinafter referred to as Hydromatrix, sold by Analytichem International (Harbor City, CA), is a diatomaceous earth porous adsorbent matrix, and is preferably used as the support carrier in this extraction process.

The extraction column 40 is then mounted into the extraction section 12. The heat exchanger 32 and extraction column 40 are then heated to desired operating temperature. The heat exchanger 32 serves to preheat the incoming SCF/modifier extraction fluid to a temperature not exceeding the desired extraction temperature. Column 40 is maintained at the operating temperature greater than the critical temperature of the SCF/modifier extraction fluid mixture.

The extraction fluids are then pumped into the extraction column 40 at a controlled rate, and the ratio of modifier to SCF is thus set by respective pump flow rates. The extraction fluids flow at specified controlled rates and the SCF combines with a modifier at a tee upstream of line 30 before entering the extraction section 12. Free flow of SCF into the extraction unit is avoided by using a spring loaded back-pressure regulator 18 set to allow flow into the extraction section 12 only at pump outlet pressures greater than the SCF cylinder pressure (830 psig at 21° C. for $CO_2$).

The pumps 22 and 26 may be operated in either constant flow rate mode or constant pressure mode. In the constant flow rate mode, the pumps stroke continuously at the set flow rates. In the constant pressure mode, the pumps stroke only when pressure in the extraction column 40 falls below the desired operating pressure.

Under the flow configuration set by valve 34 as shown in FIG. 1, the preheated extraction fluid then enters the heated extraction column 40 while valve V1 is in the off position. When the extraction column pressure has reached the desired operating value as indicated by the pressure gauge 28, valve V1 is opened to allow flow through the micrometering valve flow restrictor 36, and thereby establish dynamic flow. Fluid flow rate, or pressure if pump is operated in the constant flow rate mode, is controlled by a motor assembly mounted on valve 36.

Static extraction (no-flow) at the extraction pressure and temperature for any desired period may also be performed before establishing flow through micrometering valve 36. In this case, valve V1 is kept in the off position for a period of time to allow equilibration between the SCF mixture phase and the carbon soot phase prior to allowing flow through the micrometering valve 36 by opening valve V1. This period may be required to achieve quantitative recovery of the fullerenes if the rate of extraction is limited by the rate of desorption of the fullerenes from the carbon soot.

Following this period, valve V1 is opened. The micrometering valve 36 is kept heated at an adequate temperature to avoid clogging of the valve outlet due to freezing of the expanded fluid. The SCF loaded with fullerenes and light organic contaminants is expanded through the micrometering valve 36 to near atmospheric pressure. This pressure reduction induces a drop in the fluid density, and hence in its solvent power, thereby causing the extracted fullerenes and other contaminants to drop out of the gas mixture, and be recovered in the sample collection vessel 50. The discharged gas from the sample collection vessel 50 is vented out after passage through the gas flow meter 56.

In conventional SFE, collection vessel 50 is normally preloaded with some organic solvent and maintained at a temperature low enough to reduce the vapor pressure of the extracted contaminants and thereby avoid any significant loss of solute to the gas phase exiting the sample collection vessel 36. Since the vapor pressures of $C_{60}$ and $C_{70}$ are essentially negligible even at normally encountered extraction temperatures (31°–300° C.), collection vessel 50 may be kept at ambient temperature. However, preloading of collection vessel with an organic solvent is recommended to avoid entrainment of a fraction of the extract in the $CO_2$ by aerosol formation, and to provide a means for discharging the extract from the sample collection vessel as a liquid. The presence of an organic modifier in $CO_2$ should also aid in keeping the extract in solution following expansion.

Switching valve 34 serves to route the extraction solvent through either the SFE column 40 or the chromatography column 42. In the flow configuration wherein switching valve 34 is switched to position B, and flow through the chromatography column is established, either a conventional organic solvent such as toluene, methylene chloride, or modified supercritical $CO_2$ may be used as mobile phase. The fullerenes and contaminants recovered in the sample collection vessel 50 are introduced into the chromatography column either by manual injection, or by automatic injection or introduction of aliquots of this extract through valve 46. Automatic injection is preferred over manual injection when processing large volumes of extract.

A preferred alternative for recovering SFE extracts from the carbon soot consists of on-column trapping of the extract and subsequent fractionation of the fullerenes using Envirosep-ABC columns. This SFE-chromatographic separation interface technique using a 4-sample parallel processing apparatus is described in a copending U.S. application Ser. No. 07/727,464 filed on Jul. 9, 1991, which is herein incorporated by reference. This apparatus is used in the experiments described in examples 3 and 4. For simplicity, the other 3 identical extraction/separation sections, and details of the valves and pump controls are not shown in FIG. 1; however, the function and operation of the apparatus depicted in FIG. 1 are very similar to those of the apparatus described in the above referenced copending U.S. application.

Fractionation by predominantly adsorption chromatography results as the fullerenes and contaminants elute from the chromatography column at characteristic times. The detector 44 (ultra violet (UV), or other compatible detector) serves to monitor the purity of the fluid exiting the column, and to determine the elution time of the desired fullerene so as to collect it in a separate sample collection vessel. In cases where the detector is subject to plugging by the fullerenes, or destroys the molecular integrity of part of the effluent sample, the detector may be bypassed if the exact elution time of each compound of interest has been determined.

The column 42 can typically be a low pressure ABC S-X3 laboratory column, a high performance laboratory column such as an Envirosep-ABC, or a scaled-up version of either type of column, capable of processing larger samples than a laboratory preparative column size.

Essentially pure fractions of $C_{60}$ and $C_{70}$ are collected in sample collection vessels 50 and 52. The undesired fractions are discarded into vessel 54. Gas flow rates are preferably monitored by the flow meter 56.

The extraction and separation apparatus of this embodiment has substantially the above-described structure. A few more details will now be given.

Suitable solid phase media for use in a chromatographic separation column include a wide variety of macroreticular polymer materials or gel polymers. It is desirable that these polymers possess aromaticity, the most common of which are cross-linked polystyrenes having a molecular weight of about 100,000 to 1,000,000. Copolymers of cross-linked styrene divinyl benzene are preferred for the practice of this invention. The pore sizes of these resins can be carefully controlled by the extent to which the copolymers are cross-linked. In most applications, the higher the degree of cross-linking, the smaller the resulting pore size and, consequently, the more selective to compounds of smaller molecular size. Generally, the pore size of the cross-linked gel particles varies from about 10 to about 500 Å. Pore sizes of approximately 100 Å or less have been found to be preferred for the separations contemplated by this invention.

These gel polymers are commercially available from a number of sources in the form of small spheres or beads, usually within a particle size range of 200 to 400 mesh. A series of styrene-divinyl copolymer gels provided by Phenomenex, Inc (Torrance, CA) under the designation Phenogel, are ideally suited for use in this invention. However, other size exclusion polystyrene gel polymers may be satisfactorily used. Other suitable polymers include: Bio-Beads from Bio-Rad Laboratories, Inc. (Richmond, CA), Styragel and u Styragel from Waters Associates (Millford, MA), AMBERLITE XAD-2 and XAD-4 from Rohm and Haas Co. (Philadelphia, PA); and MicroPAK TSK Gel H from Tosohaas Company (Philadelphia, PA.).

Any organic solvent which ordinarily has a swelling effect on the cross-linked gel to be employed may be used as a medium to slurry pack the gel polymer material in the adsorption or size exclusion column. For use in swelling the cross-linked styrene-divinyl benzene resins, methylene chloride, toluene, tetrahydrofuran, or mixtures of toluene/ethyl acetate or methylene chloride/cyclohexane are preferred. These solvents can also be used as the mobile phase or as SCF modifiers for carrying the fullerenes into the chromatographic column. The SCF mixture should have a density of at least 0.6 g/cc.

Besides size exclusion, the mechanism of separation on a cross-liked polystyrene gel also includes adsorption. Indeed, separation of species of fullerenes is achieved by a combination of adsorption chromatography and steric exclusion chromatography. The adsorption chromatography is the mechanism of $\pi$—$\pi$ electron interaction of the fullerene molecules and the gel polymer resins. The steric exclusion chromatography is the mechanism of true size exclusion based on accessibility of the molecules to the pores of the gel polymer. Indeed, while $C_{70}$ is larger than $C_{60}$, $C_{70}$ is found to elute first from the column due to its stronger interaction with the PSDVB resin, indicating that adsorption effects dominate steric exclusion effects.

The chromatographic systems, other than the solvent, adsorbent and SCFs, are conventional high performance or low pressure chromatographic systems and many variations in these types and arrangement of the components of the system will be apparent to those skilled in the art.

On a laboratory scale, typically about 50 grams of suitable gel polymer particles, such as Phenogel, are slurried in 200 to 400 ml of toluene or any other adequate solvent, and the mixture is allowed to stand for about 18 to 24 hours at room temperature to expand or swell the polymer. The resulting gel is then poured or suitably introduced into a chromatographic column.

The toluene-polymer gel, prepared as described above, is sealed in a chromatographic column. An organic solvent, SCF or mixture thereof is introduced into the top of the chromatographic column together with a sample of fullerenes and contaminants to be separated. As the mixture moves down the column the smaller molecules $C_{60}$ are separated from $C_{70}$; however, as a result of stronger $\pi$—$\pi$ electronic interactions between $C_{70}$ molecules and the resin which result in greater retardation of the $C_{70}$ molecules, $C_{60}$ actually elutes before $C_{70}$. Essentially pure $C_{60}$ and $C_{70}$ fullerenes are recovered separately, and may be concentrated by evaporation of the mobile phase.

The column length can vary with different flow rates and mobile phase components, however lengths of about 50 mm to about 450 mm produce good separation results. Suitable column inside diameters range from 5 mm to 50 mm.

Suitable mobile phase flow rates for either liquid or SCF mobile phases range from about 0.5 ml/min to 20 ml/min. The concentration of the mixture of fullerenes in the mobile phase ranges from 0 to 4 mg/ml, preferably 0.1 to 4 mg/ml.

Note that while the preferred mode of the present invention displays an efficacy of combined SFE and chromatographic separation to provide essentially pure $C_{60}$ and $C_{70}$ fullerenes from carbon soot, the chromatographic separation and SFE columns (i.e., O.D., I.D., and length), and other extensive parameters such as mobile phase and SFE solvent flow rates, and associated valves and tubing, may be properly scaled to larger sizes in order to increase the processing capacity of the extraction and separation unit to industrial quantities.

FIGS. 2 to 5 depict the UV spectrum of a mixture of fullerenes that have been separated according to the procedures of the present invention as well as the UV spectrum of each compound. These analyses are more fully discussed in the following examples, but it is noted from these analyses that a clear separation is made between $C_{60}$ and $C_{70}$ fullerenes and that they can be easily identified and recovered.

Reference is now made to the following examples illustrating specific embodiments of the present invention.

EXAMPLE 1: DETERMINATION OF FULLERENE UV SPECTRA AND RESPONSE FACTORS

The weight response factors of $C_{60}$ and $C_{70}$ were determined in the following manner. Given the unavailability of pure $C_{60}$ or $C_{70}$ reference standards, a mixture of unknown composition of $C_{60}$ and $C_{70}$ in toluene was first prepared, and the total weight of $C_{60}$ and $C_{70}$ in 1 ml of this mixture was determined by evaporation of the solvent. The UV spectra of $C_{60}$ and $C_{70}$ were then determined. The response factors for $C_{60}$ and $C_{70}$ at 330 nm were established by assuming that the UV molar absorptivity of $C_{60}$ and $C_{70}$ are equal in the 260 nm±40 nm range. This assumption is acceptable because of the low concentration of $C_{70}$ in the sample and the wide absorption band around 260 nm.

Two Envirosep-ABC PSDVB columns, available from ABC Laboratories, Inc., 300 mm long, and having column I.D. of 7.8 mm and 22.5 mm respectively, were equilibrated with methylene chloride, and eluted with methylene chloride at 2 and 5 ml/min respectively. The pore size of the PSDVB resin was 50 Å.

A sample of a mixture of desired fullerenes was prepared by thorough mixing of three (3) mg of a mixture of $C_{60}$ and $C_{70}$ fullerene compounds in seven (7) ml of methylene chloride. The sample was then allowed to equilibrate. A 50 μl sample of this solution was injected into each column respectively. Column temperatures were 40° C. Each column was evaluated individually for detection and separation of the $C_{60}$ and $C_{70}$ mixture by monitoring the UV absorption at 240 nm as this wavelength provided maximum sensitivity for the $C_{70}$ compound. A Hewlett Packard 1090 series HPLC system equipped with a photodiode array detector was used for mobile phase delivery and detection. Two peaks were observed on each column and each peak was collected individually. Approximately 45 HPLC runs using the 7.8 mm i.d. ×300 mm O.D. column were conducted.

Figure 2:
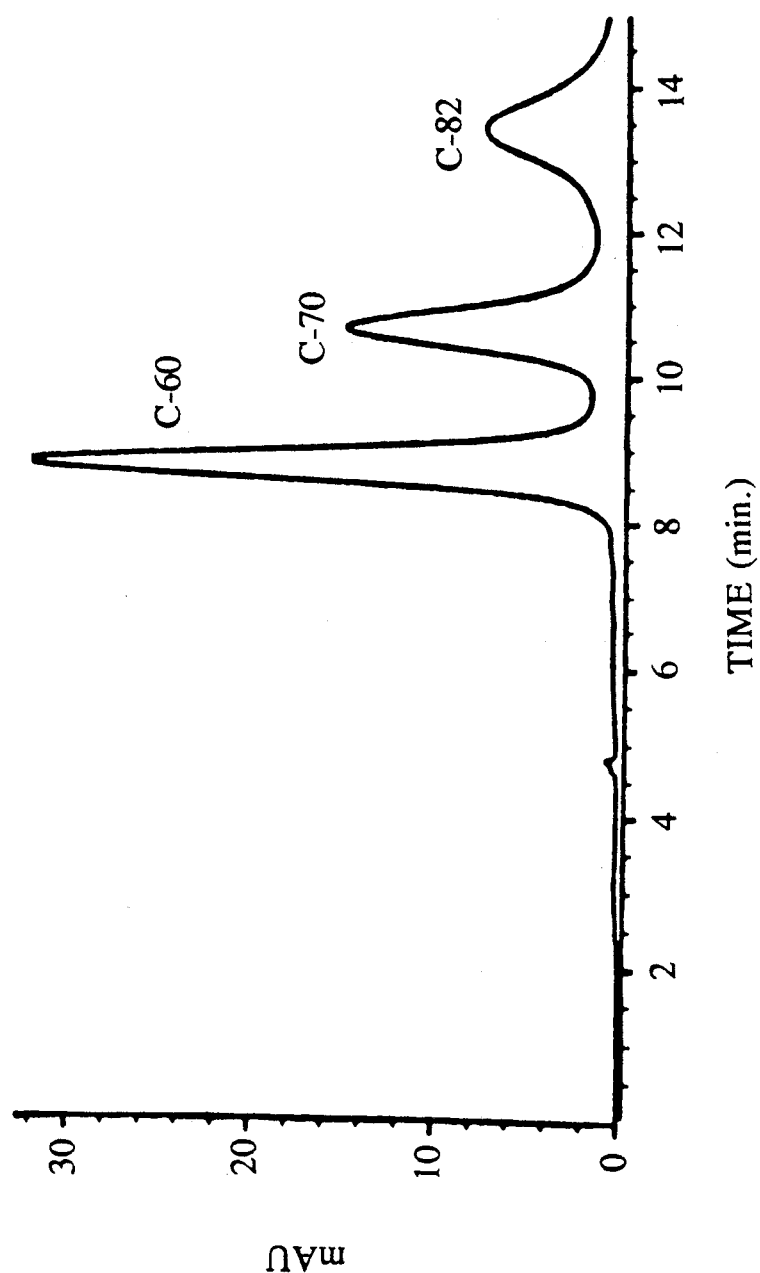
FIG. 2 is a representative chromatogram for fullerene materials ($C_{60}$, $C_{70}$ and $C_{82}$) fractionated with a 7.8 mm I.D. Envirosep-ABC (ABC Laboratories Inc., Columbia, MO) column in accordance with the purification method of this invention. Methylene chloride mobile phase flow rate was set to 2 ml/minute.
Figure 3:
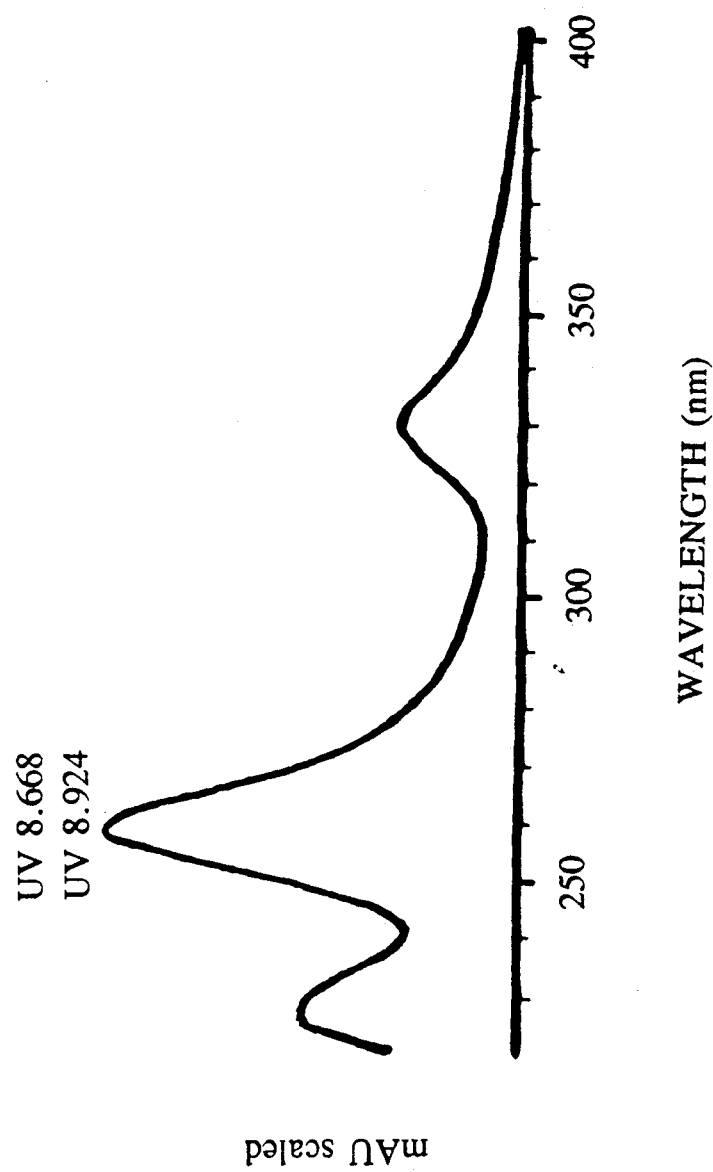
FIG. 3 is the UV spectrum of $C_{60}$.
Figure 4:
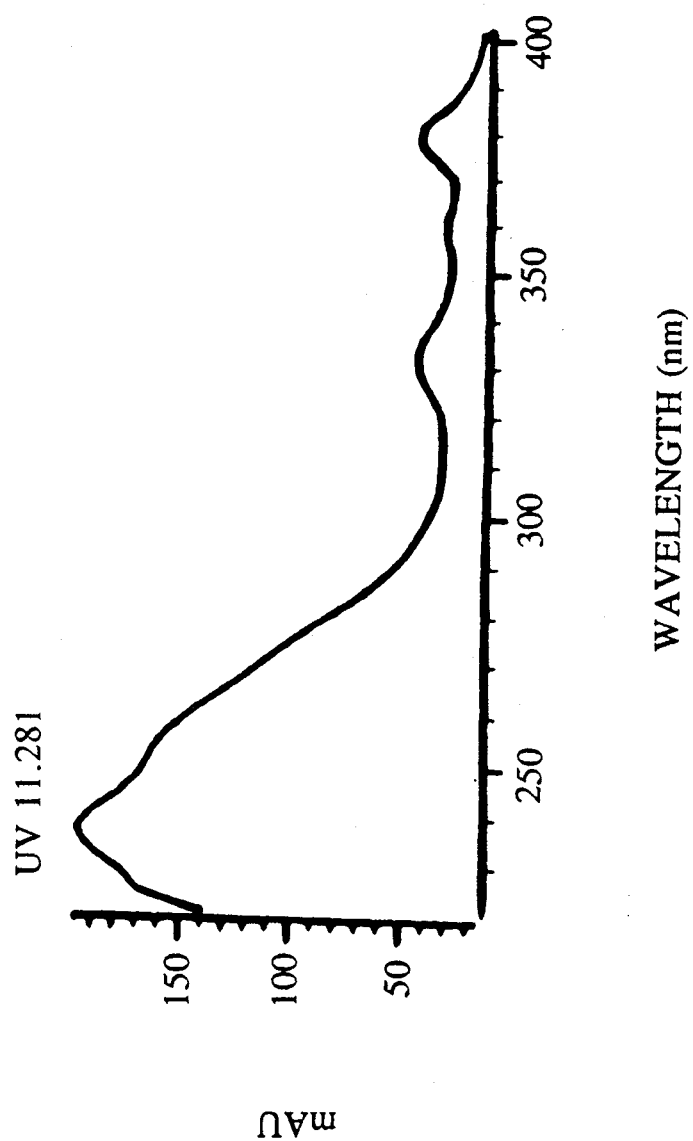
FIG. 4 is the UV spectrum of $C_{70}$.

As shown in FIG. 2 the elution time for $C_{60}$ (peak one) and $C_{70}$ (peak two) from the 7.8 mm I.D. column are 8.93 minutes and 11.28 minutes respectively. This reversed size exclusion elution order indicates that the retention mechanism of $C_{60}$ and $C_{70}$ on an Envirosep-ABC column is not by size exclusion ($C_{70}$ has a larger molecular volume than $C_{60}$, diameter ca. 10 −15 Å). The most plausible mechanism for the separation of $C_{60}$ and $C_{70}$ is an instantaneous dipole-induced dipole interaction. The high polarizability of π-electrons, from the continuous electron density fluctuation, results in especially strong dispersion forces among molecules with conjugated π-electron systems (i.e., the aromatic π electrons of $C_{60}$ and $C_{70}$ molecules interact with the π-electrons of the PSDVB stationary phase). Thus, elution order indicates that adsorption chromatography dominates exclusion chromatography, and that the greater aromaticity of $C_{70}$ with respect to $C_{60}$ induces adsorption forces that are significant enough to overcome steric effects, and alter the expected elution profile from a conventional size exclusion column. The UV spectrum for the recovered fullerenes is shown for $C_{60}$ in FIG. 3 and for $C_{70}$ in FIG. 4.

The eluate containing the first peak ($C_{60}$) bore a purple color and had a UV spectrum similar to that of a reference spectrum for $C_{60}$. The eluate containing the second peak ($C_{70}$) bore a rose-violet color, and exhibited a similar spectrum as a reference spectrum of $C_{70}$ in the region of 220–400 nm. The ratio of the two peaks did not change significantly throughout the chromatographic analyses.

Figure 5:
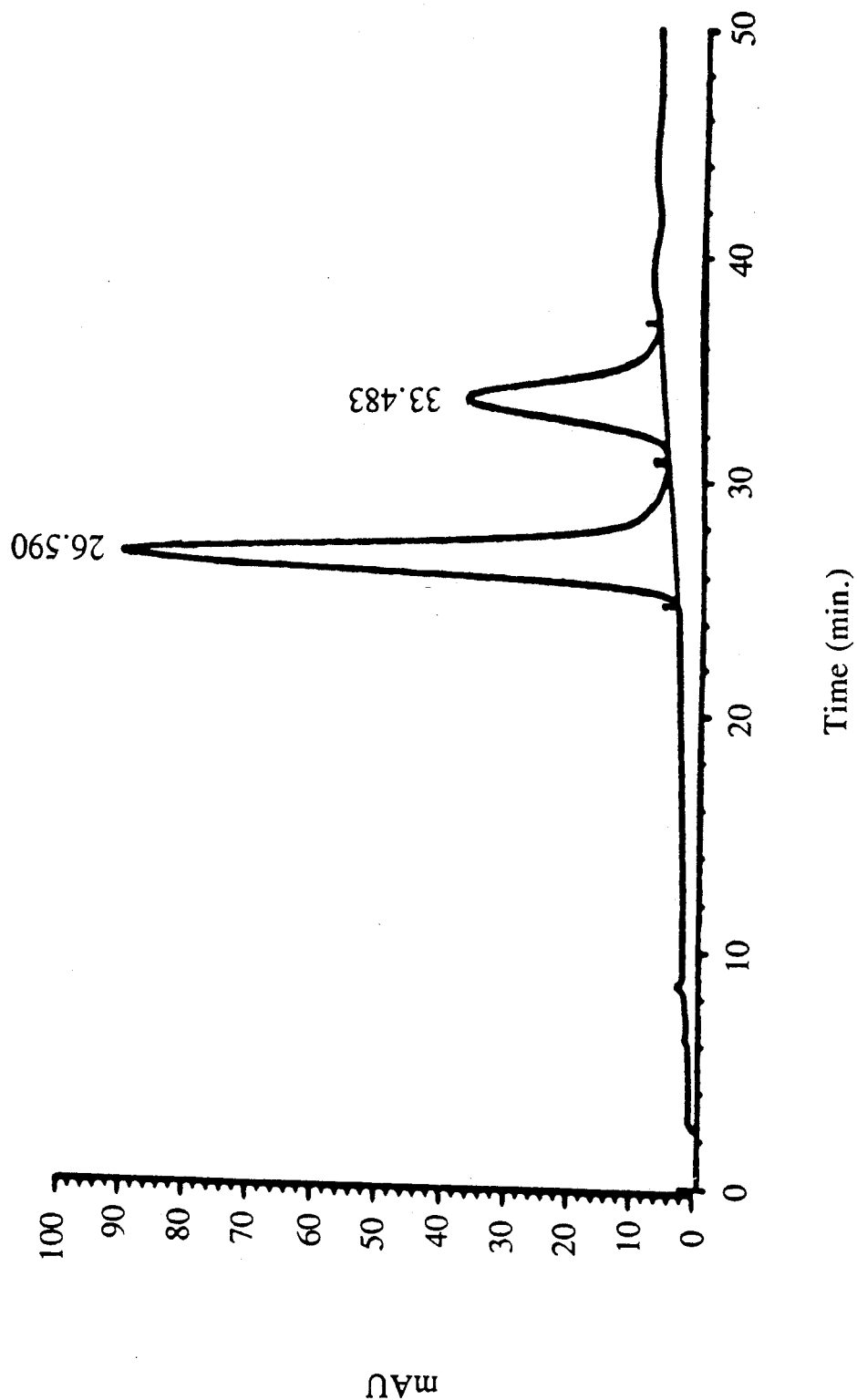
FIG. 5 is a representative chromatogram for fullerene materials ($C_{60}$ and $C_{70}$) fractionated with a 22.5 mm I.D. Envirosep-ABC column in accordance with the method of this invention. Methylene chloride mobile phase flow rate was set to 5 ml/minute.

Results obtained with the 22.5 mm I.D. column are shown in FIG. 5. This column has a larger processing capacity than the 7.8 mm I.D. column. Typically, 2 ml of saturated solutions of $C_{60}$ and $C_{70}$, corresponding to roughly 8 mg of fullerenes, are well separated by this column. Retention times are, however, longer. Details of optimization of the chromatography separation are set forth in examples 5 and 6.

EXAMPLE 2: SEPARATION OF FULLERENES $C_{60}$ AND $C_{70}$ FROM REACTION PRODUCTS

Figure 6:
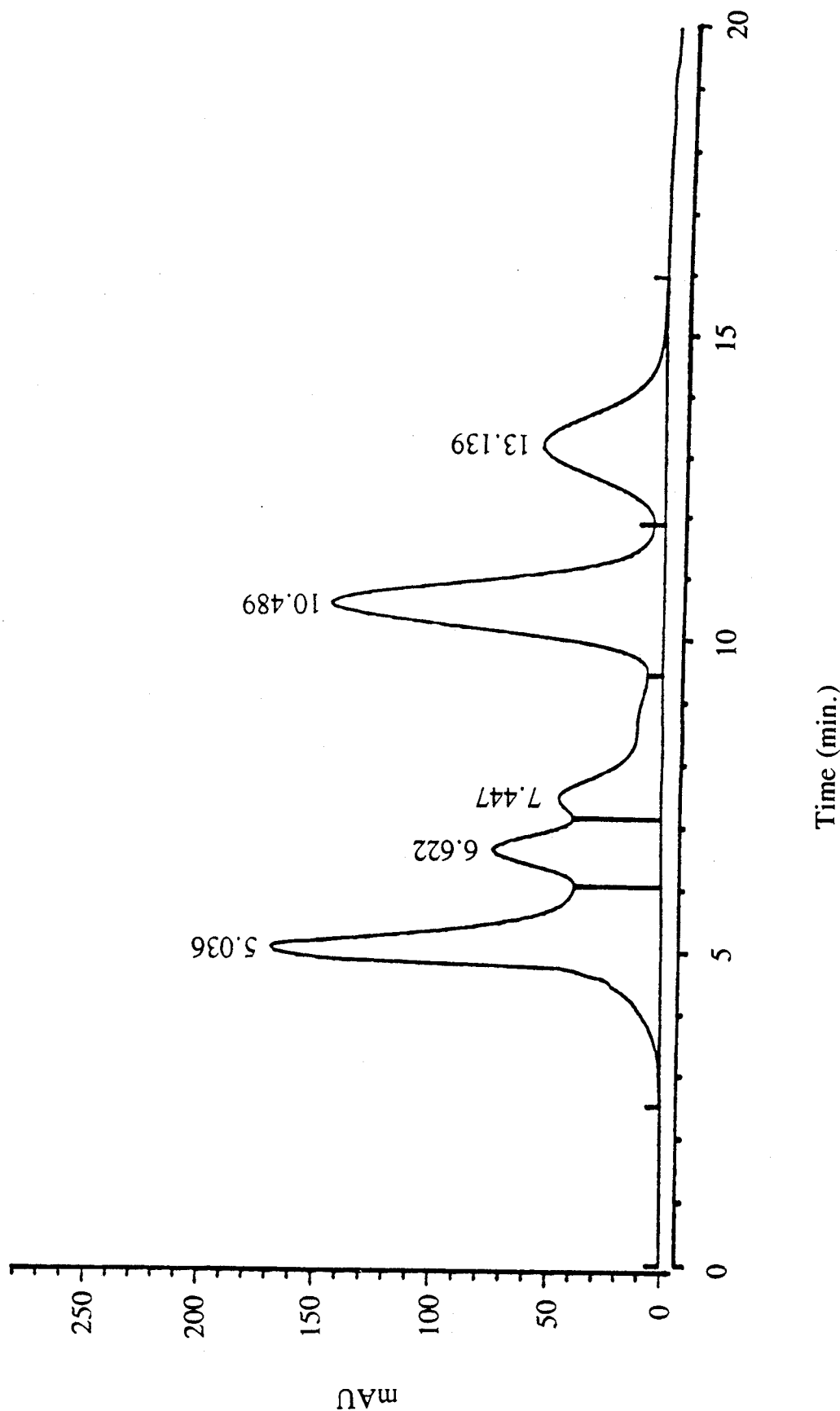
FIG. 6 is a chromatogram illustrating the separation of $C_{60}$ and $C_{70}$ from their epoxidation products.

Substituted fullerene products obtained by bromination and epoxidation of $C_{60}$ and $C_{70}$ are also well separated from their parent compounds. FIG. 6 shows the UV HPLC chromatogram of the product of epoxidation of a $C_{60}/C_{70}$ mixture in a methylene chloride/toluene solution. The sample was eluted with methylene chloride mobile phase through a 50×7.8 mm Envirosep-ABC guard column and a 300×7.8 mm Envirosep-ABC column disposed in series. The first peak at 5.04 minutes corresponds to toluene, while reaction products include the 6.62 and the 7.45 minute peaks. The product eluting at 6.62 minute was identified as $C_{60}NO_6$. The reaction products are thus well separated from the reactants $C_{60}$ and $C_{70}$ which elute at 10.49 and 13.14 minutes respectively. The shorter retention times of reaction products as compared to the parent compounds is due to lower aromaticity of the reaction products. This is brought about by breakup of πi—πi bonds by addition reactions.

The following 2 examples illustrate the effects of temperature, pressure, and nature and concentration of modifier on recovery and selectivity of SCF extraction (SFE) towards fullerenes. Raw carbon soot samples obtained from MER corporation were extracted by sonication into toluene and were determined to contain 5.86%±0.09% $C_{60}$ and 0.78%±0.05% $C_{70}$ by weight.

EXAMPLE 3: SFE WITH PURE $CO_2$ AND MODIFIED $CO_2$ WITH 8.6 MOLE % CYCLOPENTANE AND 14.0% MOLE % TOLUENE

The ability of supercritical $CO_2$, and SCF mixtures of cyclopentane and toluene in $CO_2$ to selectively extract soluble fullerenes from carbon soot samples was assessed at different pressures and temperatures. The carbon soot samples and Hydromatrix were loaded into the columns by the pour and tap method as follows : 0.259 g and 0.255 g of carbon soot samples mixed with Hydromatrix, and sandwiched between two layers of Hydromatrix, were poured and tapped into columns 2 and 3 respectively. The column content was then covered with a paper filter and a 4" long cylindrical stainless steel (ss) annular rod. Total quantity of Hydromatrix used per column amounted to about 28 grams. The ss rod is used to uniformly compact the sample and Hydromatrix so that equal resistance flow channels through the column are established. The filter paper is used to provide a flat base for the compaction rod.

The SFE runs were conducted with a multiple sample SFE-HPLC unit that is a multiple column version of the unit shown in FIG. 1. This unit allows for simultaneous extraction of up to 4 samples of 100 grams or less, and provides independent temperature, pressure, and flow rate control for each of the 4 extraction columns and 4 metering valves. The unit permits delivery of a liquid modifier at specified volume ratios by means of controlling the number of pump strokes for both $CO_2$ and modifier. Heated metering valves are maintained at the same temperature as the respective columns. Sample collection vessels were kept cool at around 0° C. by immersion in water cooled with dry ice. A more detailed description of this instrument and its modes of operation are given in the Ser. No. 07/727,464.

(1) SFE with $CO_2$

Samples 2 and 3 were first extracted with 5 ml/min of supercritical $CO_2$ for about 75 minutes at a pressure of 7,500 psi and at temperatures of 90° C. and 60° C. respectively. Analysis of extract showed no detectable amounts of fullerenes, and no apparent difference in the nature of extracted lower molecular weight compounds.

The inability of pure $CO_2$ to extract the fullerenes is attributed to its low solvent power and its low degree of interaction with the electronic cloud of the 5- and 6-carbon ring units composing fullerene molecules. Hence, addition of a modifier is required to effect measurable recoveries of fullerenes.

(2): SFE with 8.6 mole % cyclopentane/$CO_2$ mixture

Cyclopentane was then employed $CO_2$ modifier (8.6 mole %) to determine the effect of a slightly better solvent on recovery. Although it is not expected to significantly enhance recovery due to its lack of aromaticity and polarity, cyclopentane molecule being planar should provide greater wetting and interaction with the fullerenes than $CO_2$, and thereby increase their recovery.

Figure 7A:
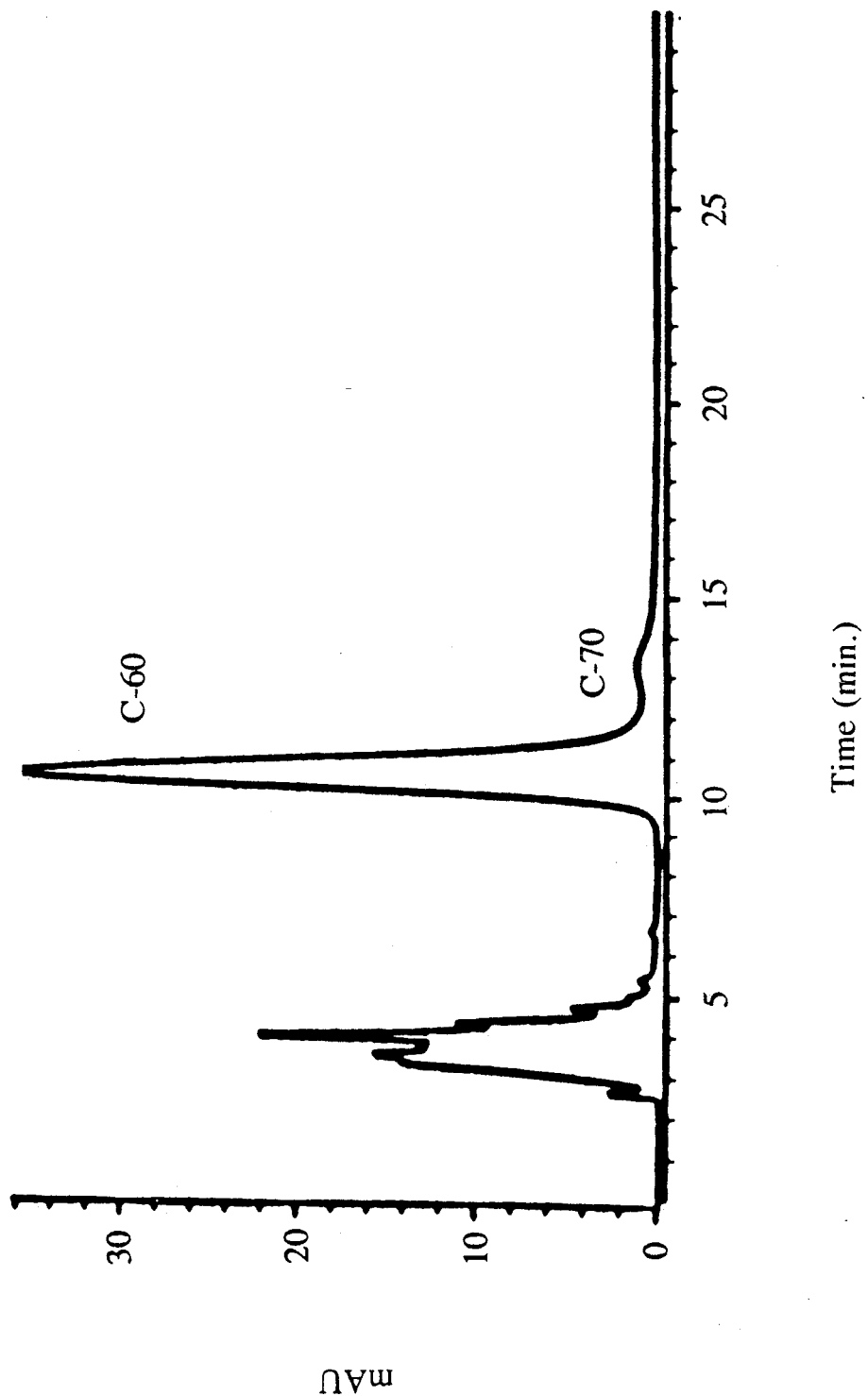
FIGS. 7a and 7b illustrate the selective extraction of $C_{60}$ from carbon soot with a supercritical $CO_2$/cyclopentane mixture.
Figure 7B:
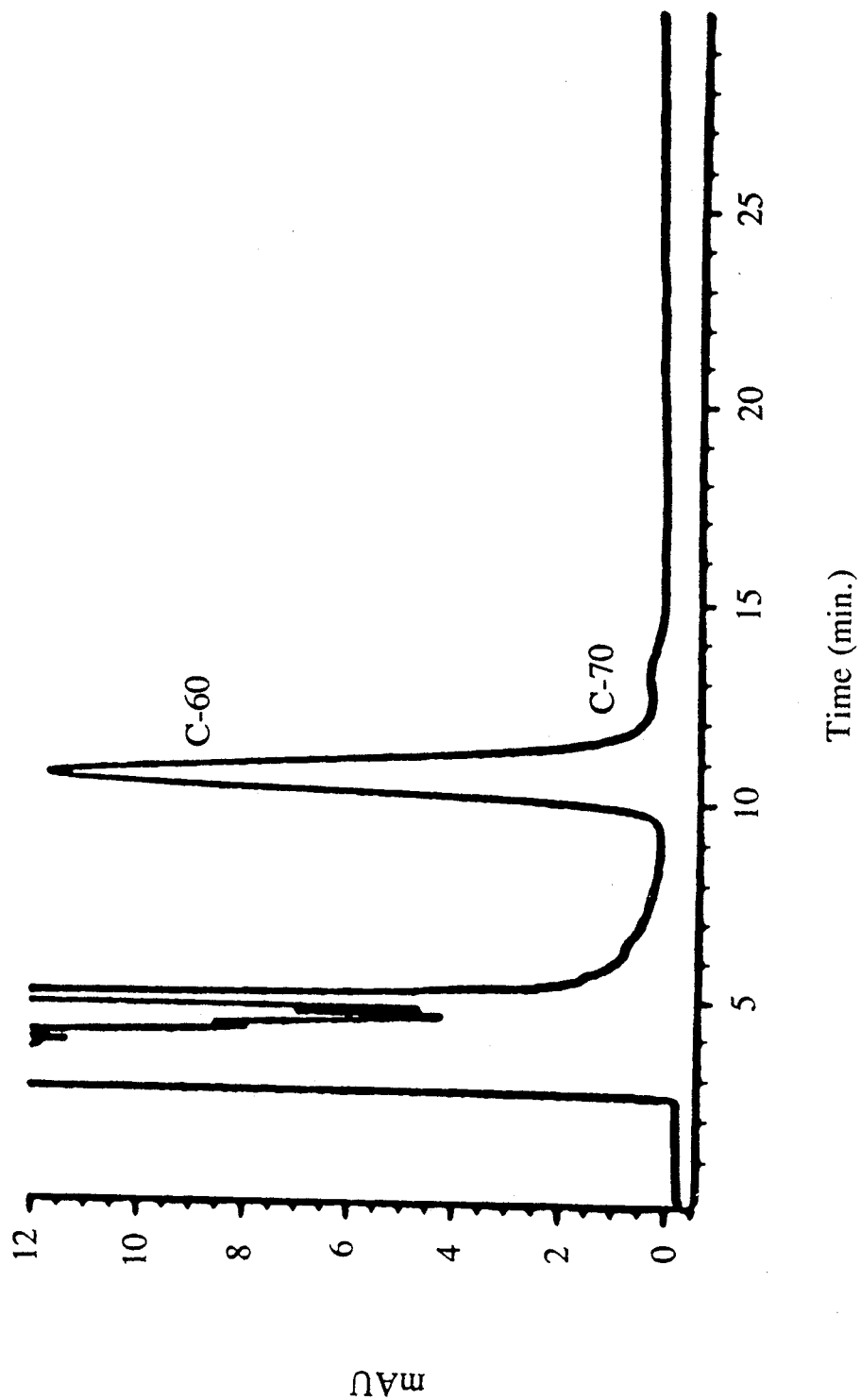

Samples 2 and 3 were then re-extracted with 2.5 ml/min of this mixture for 75 minutes at a pressure of 7,500 psi and at temperatures of 90° C. and 110° C. respectively. These conditions are supercritical since Tc and Pc of this solvent mixture, evaluated using the Peng-Robinson equation of state (P-R EOS) and the Gibbs criteria for critical points (Saim and Subramaniam, *Chem. Engr. Sci.*, 43, 1837, 1988), with a binary interaction parameter of 0.1, are determined to be 57° C. and 1340 psi respectively. FIGS. 7a and 7b shows the UV chromatograms of the concentrated extracts of samples 2 and 3 respectively, obtained using a 50×7.8 mm Envirosep guard column in line with a 300×7.8 mm column. Fullerene $C_{60}$ extracts from samples 2 and 3 amounted to 13.1 μg and 7.8 μg respectively. The amount of lower molecular weight compounds extracted from sample 3 is appreciably higher than from sample 2 due to its higher extraction temperature. Thus, while solubility of low molecular weight compounds increased with increasing temperature due to their relatively high volatility, solubility of the fullerenes decreased with increasing temperature, as is expected for SFE of solids at temperatures well below their melting points. Little $C_{70}$ was extracted from either sample, indicating that a high selectivity for $C_{60}$ can be achieved under these extraction conditions. This example illustrates the ability of this mixture to selectively extract $C_{60}$ from the soot mixture. Recovery can be increased by optimizing pentane content in the mixture, pressure, temperature, and extraction time.

(3): SFE with 14 mole % toluene/$CO_2$ mixture

Since only a small quantity of fullerenes has been extracted by the previous process, it is assumed that the soot samples fullerene contents are essentially unaltered by the previous extraction runs. In order to enhance recovery of the fullerenes, a mixture of roughly 14 mole % toluene in $CO_2$ was employed as SFE solvent. Toluene was selected as $CO_2$ modifier because of its high affinity for fullerenes brought about by dipole-induced dipole interaction between the pi electron clouds of toluene and the fullerenes.

Based on simple Kay's rules (Walas, S.M. *"Phase Equilibria in Chemical Engineering"*, Butterworth, 1986, p. 29), this mixture has a critical temperature of about 71° C. (344 K.). The critical temperature and pressure of this mixture, evaluated using the Gibbs energy minimization method and the P-R EOS with a binary interaction parameter of 0.1, were determined to be 88° C. (361 K.) and 2,137 psi respectively.

The effects of pressure and temperature on recovery was investigated by simultaneous extraction of each of samples 2 and 3 for successive periods of 30 minutes at pressures of 4,000, 5,000, 6,000, 7,000 and 7,500 psi. Transition to a new pressure level consisted of shutting off column flow at the end of the extraction period, allowing pressure in the column to reach the new level, and then re-establishing flow at the desired rate. Samples 2 and 3 were re-extracted at temperatures of 70° and 110° C. respectively. Sample 2 was thus extracted at a temperature below the critical temperature of the solvent mixture and, hence, the concentration of toluene in the supercritical fluid phase was lower than 14% (about 11%). Except for a static period of 20 minutes between the extractions at 4,000 and 5,000 psig, all extractions were dynamic at 2.5 ml/min of saturated liquid $CO_2$ at ambient temperature.

Figure 8:
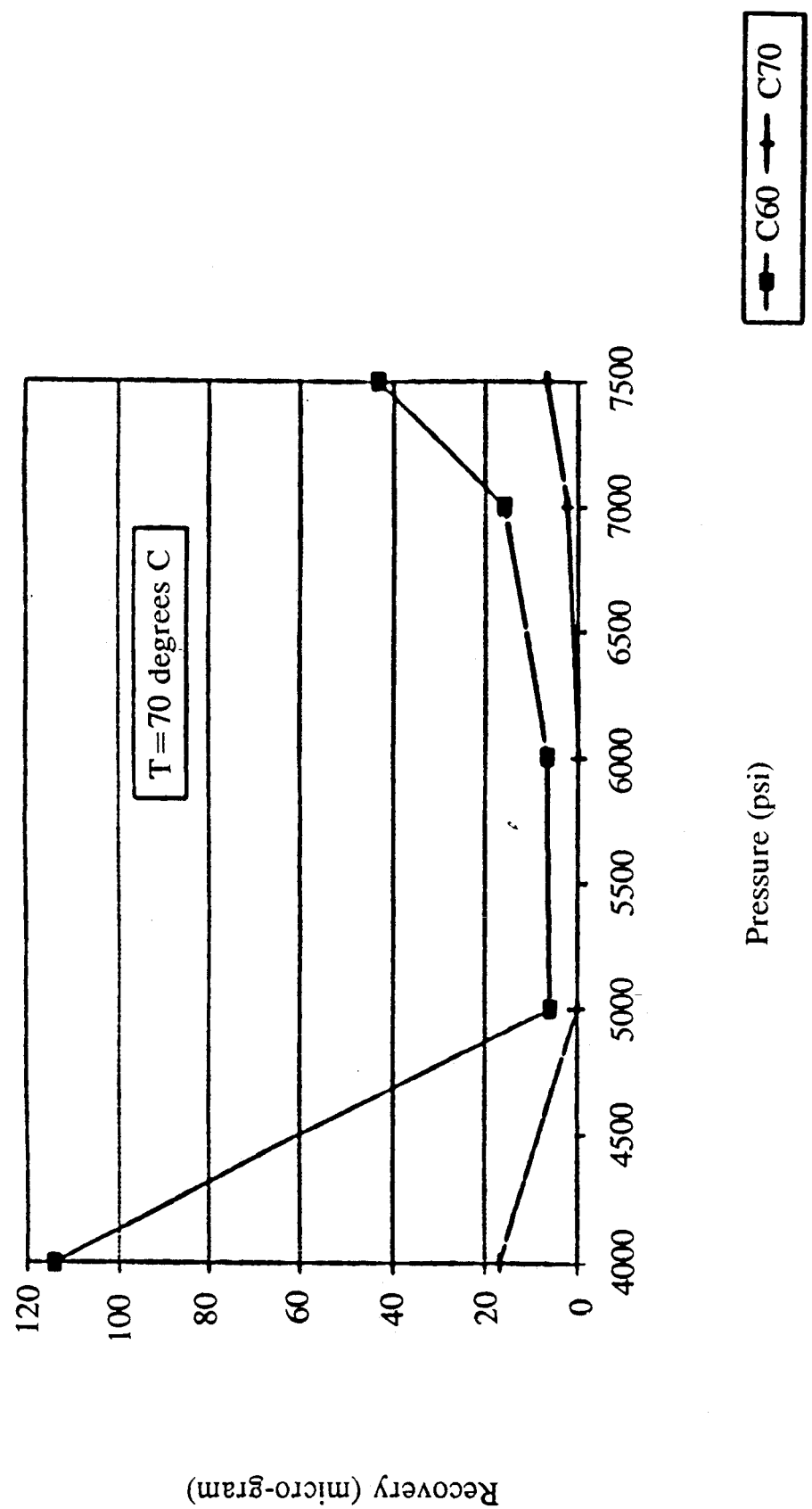
FIGS. 8 and 9 illustrate the effects of temperature and pressure on SFE recovery of fullerenes $C_{60}$ and $C_{70}$.
Figure 9:
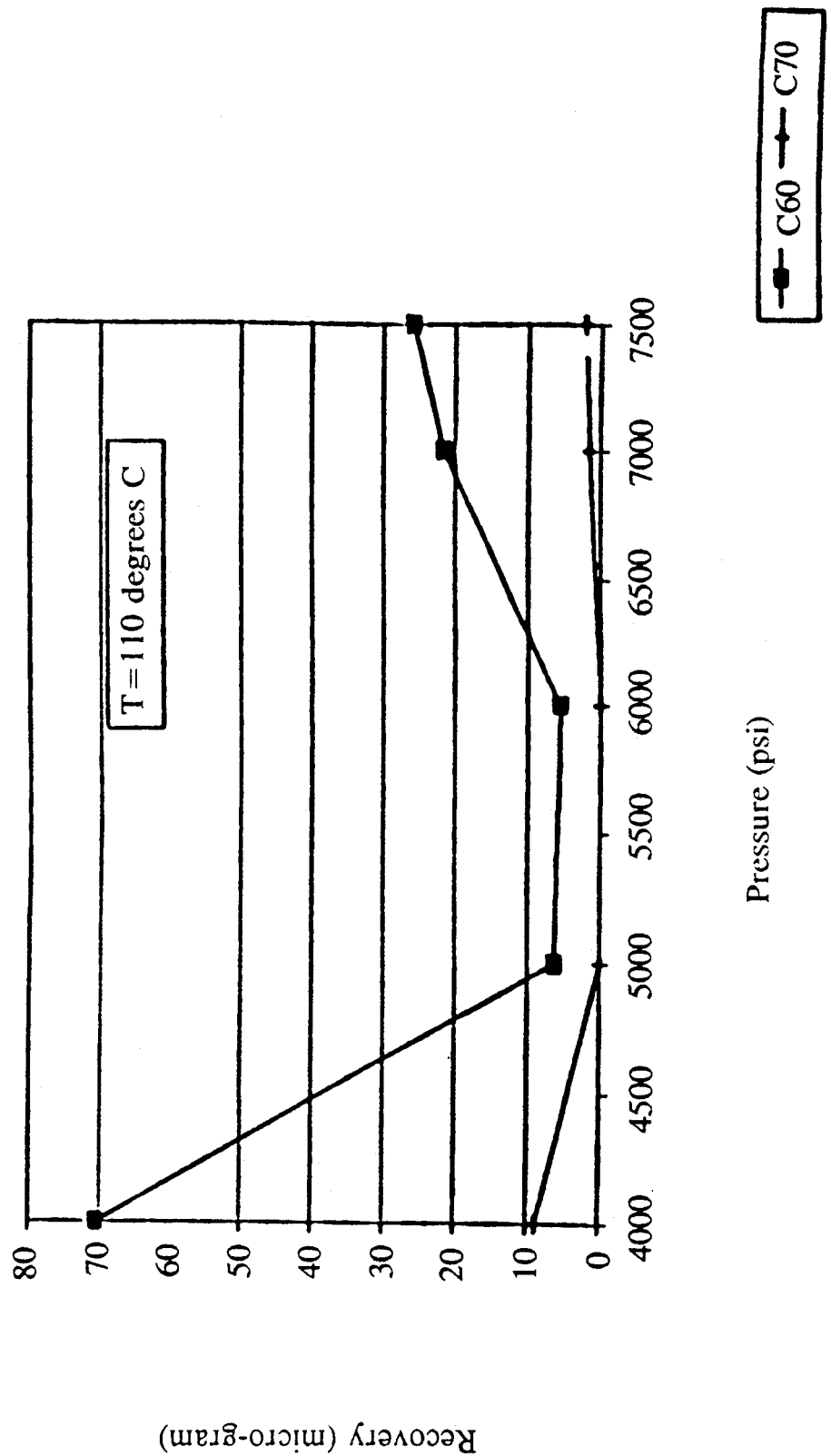

Analysis of UV chromatograms of extracts shows that the ratio of extracted $C_{60}/C_{70}$ at all pressures is close to the ratio in the original carbon matrix (about 7/1), indicating that little selectivity is achieved with this extraction mixture under these conditions. FIGS. 8 and 9 show the change in recovery of $C_{60}$ and $C_{70}$ from samples 2 and 3 respectively. It is noted that these recoveries show the same trend with temperature as with extraction with the cyclopentane/$CO_2$ mixture; however, though still low, recoveries are higher than those exhibited in the previous runs using the cyclopentane/$CO_2$ mixture.

The precise reasons for the decrease in recovery between 4,000 and 6,000 psig are not known, but it may be speculated that it is due to an increase in mass transfer resistance brought about by both the increased viscosity of the solvent and the reduced diffusivity of the solvent and fullerenes, as well as the ensuing lowering of the vapor pressure of the fullerene molecules. Also, the closeness of the extraction temperatures of the solvent mixture to its critical temperature may also cause a change in the phase behavior of the solvent/fullerene mixture which could engender such effects. These effects appear to be slightly overcome as pressure reaches 6,000-7,000 psig. The density of the solvent mixture at 110° C. in this pressure range is 0.80-0.84 g/c. Thus, it appears that around this pressure range, the reduction in transport properties and vapor pressure brought about by the increased pressure is now compensated by the increase in solvent power.

EXAMPLE 4: SFE WITH A MIXTURE OF 8.8 MOLE % TOLUENE IN $CO_2$

The effect of pressure on the ability of a more dilute SCF mixture of toluene in carbon dioxide (8.8 mole % toluene) to selectively extract $C_{60}$ from the carbon soot matrix was evaluated. The critical temperature and pressure of this mixture, evaluated using the Gibbs energy minimization method and the P-R EOS, are determined to be 63° C. (336 K.) and 1,616 psi respectively. Operation at 110° C. (383.2 K.) and 5,000 psig corresponds to operation at a reduced temperature of 1.16, and a reduced pressure of 3.33, values that are well above the critical point. The density of this mixture, evaluated using the P-R EOS, is equal to 0.71 g/cc.

In these runs, column 1 was not used, column 4 was filled with blank Hydromatrix to determine whether any cross-contamination between samples occurs, and columns 2 and 3 were loaded with carbon soot samples and Hydromatrix by the pour and tap method as described previously. Both samples 2 and 3 consisted of 45 mg of soot thoroughly mixed with 1 gram of Hydromatrix material.

Flow rate through column 2 was difficult to control due to plugging of the metering valve with extracted material, and required constant supervision and adjustment of the micrometering valve flow opening. Flow rate through columns 3 and 4 were easily controlled. The better flow control through column 3 was achieved by adding a soft seat micrometering valve downstream the expansion micrometering valve. Flow through column 4 was easily controlled because no material that would temporarily restrict flow through the micrometering valve was being extracted.

Figure 10A:
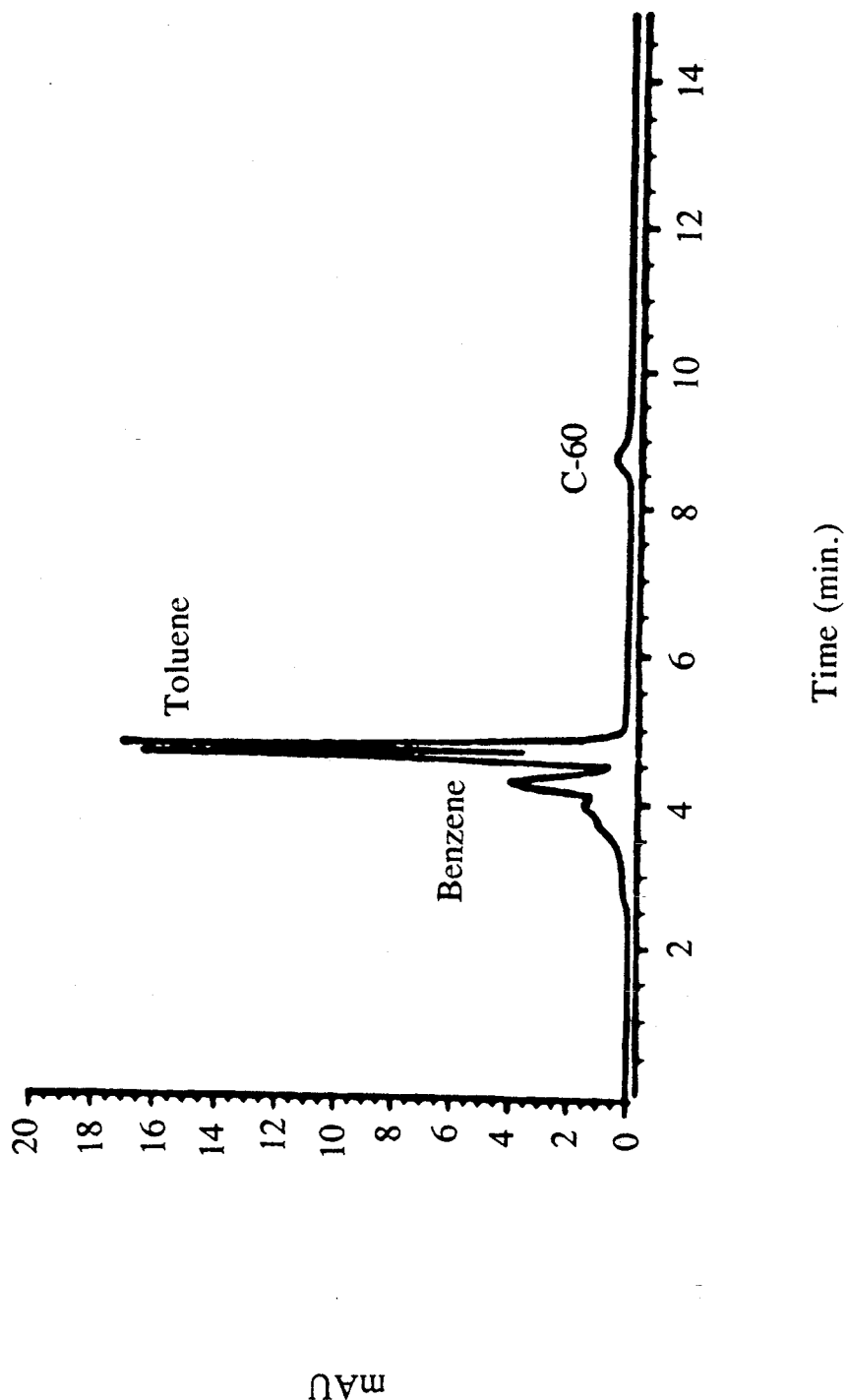
FIGS. 10a, 10b and 10c illustrates recovery of fullerenes $C_{60}$ and $C_{70}$ at 5,000 psig, 110° C. with a dilute mixture of toluene in $CO_2$.
Figure 10B:
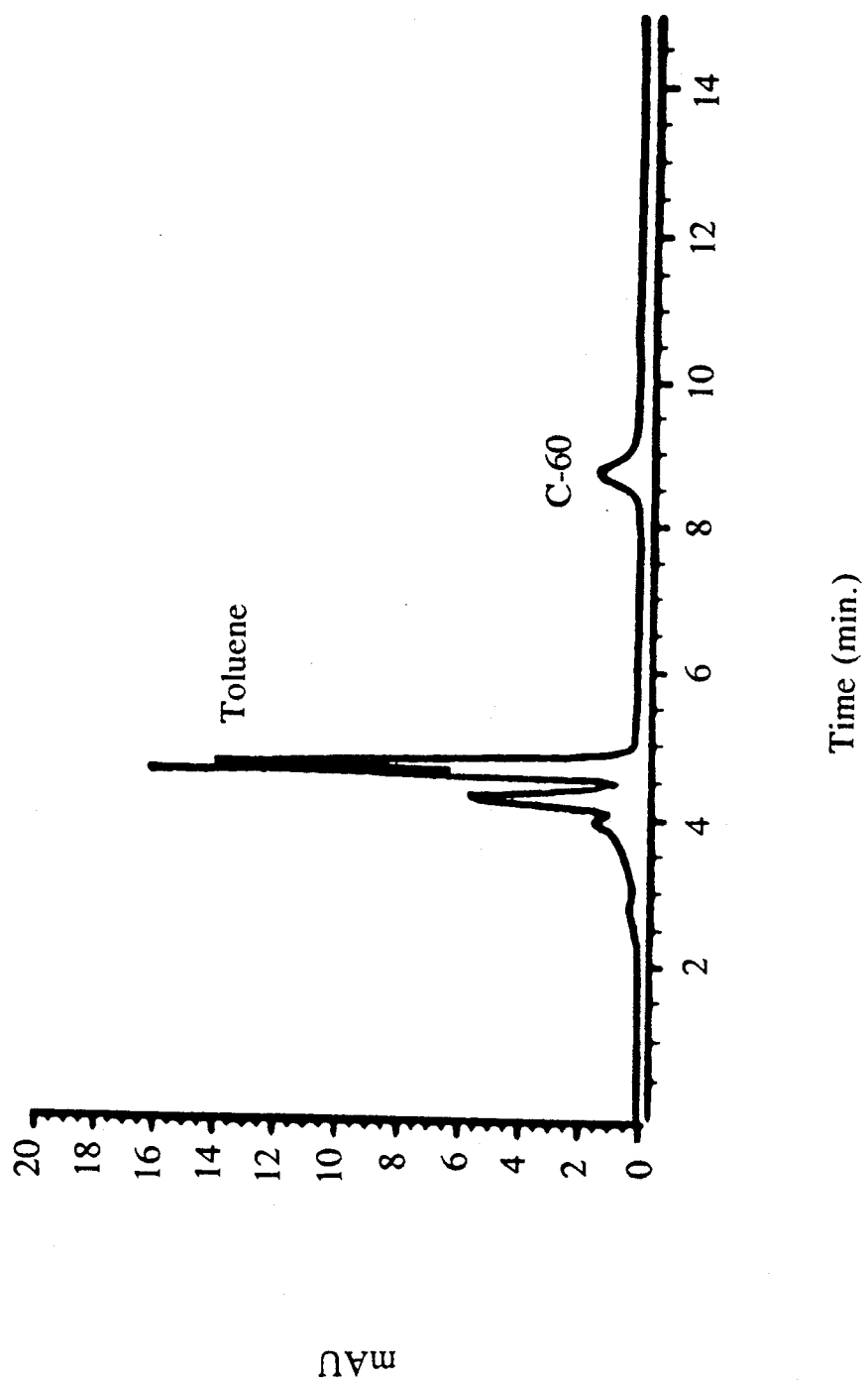
Figure 10C:
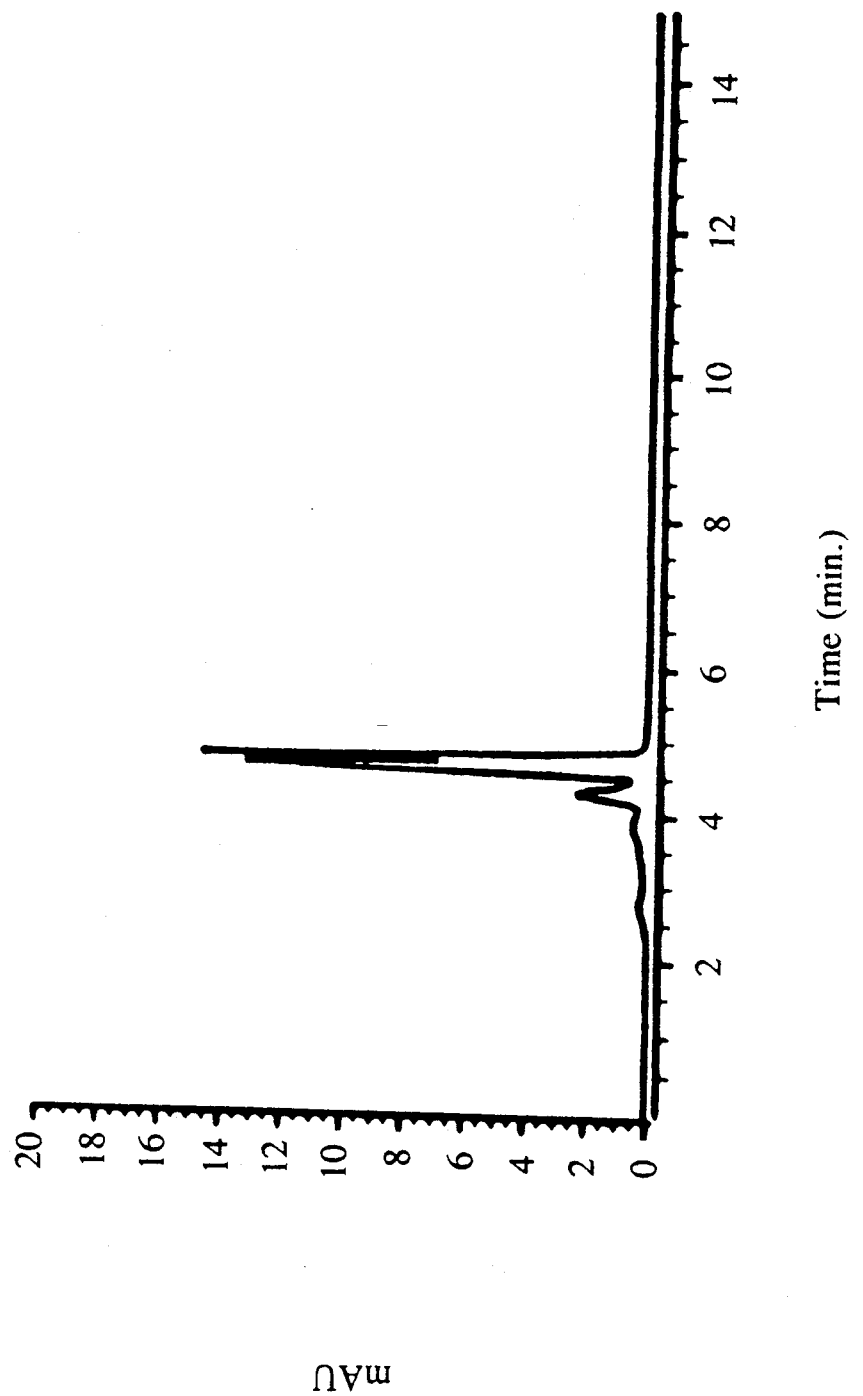

SCF mixture flow rates through columns 2, 3 and 4 averaged 2.3, 2.3 and 3.2 ml/min respectively. Flow rate through column 4 was monitored by an electronic flow meter. Continuous flow through columns 2, 3 and 4 was maintained for 75 minutes. Total volumes of toluene solutions of extracted material (mainly $C_{60}$, $C_{70}$ and lower molecular weight contaminants) in columns 2, 3 and 4 amounted to 40 ml, 40 ml, and 56 ml respectively. FIGS. 10a, 10b and 10c and Table 1 show the UV chromatograms of the three SFE samples and fullerene recovery results from this run respectively.

TABLE 1

| Extraction of $C_{60}$ and $C_{70}$ from a Carbon Soot at Supercritical Conditions (5,000 psig. 110° C.). | | | | | |
|---|---|---|---|---|---|
| Sample or Column Number | $C_{60}$ in Sample (mg) | $C_{70}$ in Sample (mg) | Recovery of $C_{60}$ (mg) | Recovery of $C_{70}$ (mg) | Recovery of $C_{60}$ (%) |
| 2 | 2.64 | 0.35 | 0.0224 | N.D. | 0.85 |
| 3 | 2.64 | 0.35 | 0.0650 | N.D. | 2.46 |
| 4 | 0 | 0 | N.D. | N.D. | N.D |

(N.D.: Not Detected.)

It is evident from Table 1 that the SCF mixture was unable to quantitatively extract $C_{60}$ or $C_{70}$ from the carbon soot. $C_{60}$ concentrations in SFE extract samples 2 and 3 ($0.5 \times 10^{-3}$ and $1.6 \times 10^{-3}$ mg/ml) are small compared to its solubility in liquid toluene ($\approx 3.8$ mg/ml).

Several factors may have contributed to this low recovery, including the low density of the SCF (0.73 g/cc) which may be below the threshold solubility density of either fullerene, and the short residence time of the SCF phase in the section of the column housing the carbon soot (about 40 seconds for samples 2 and 3). The difference in recovery between samples 2 and 3 is believed to be due to the somewhat erratic flow rate through column 2. It is interesting to note, however, that essentially no $C_{70}$ was recovered in either sample, indicating the possibility of fractionation of the extractable material by selective extraction of $C_{60}$. No cross-contamination between samples occurred throughout the run as evidenced by the purity of the extract from sample 4 (blank sample).

Figure 11A:
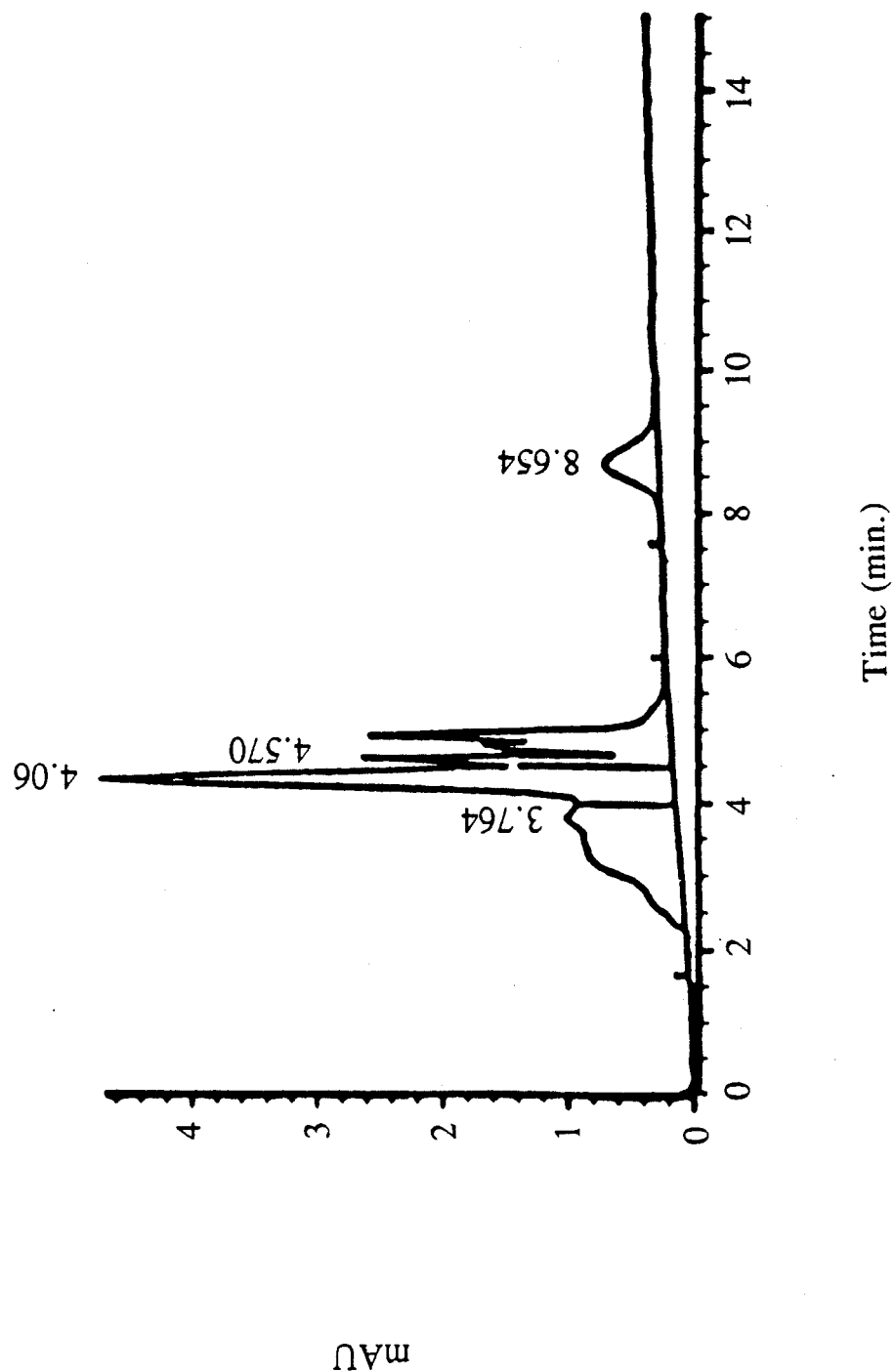
FIGS. 11a, 11b and 11c illustrates recovery of fullerenes $C_{60}$ and $C_{70}$ at 7,000 psig, 110° C. with a dilute mixture of toluene in $CO_2$.
Figure 11B:
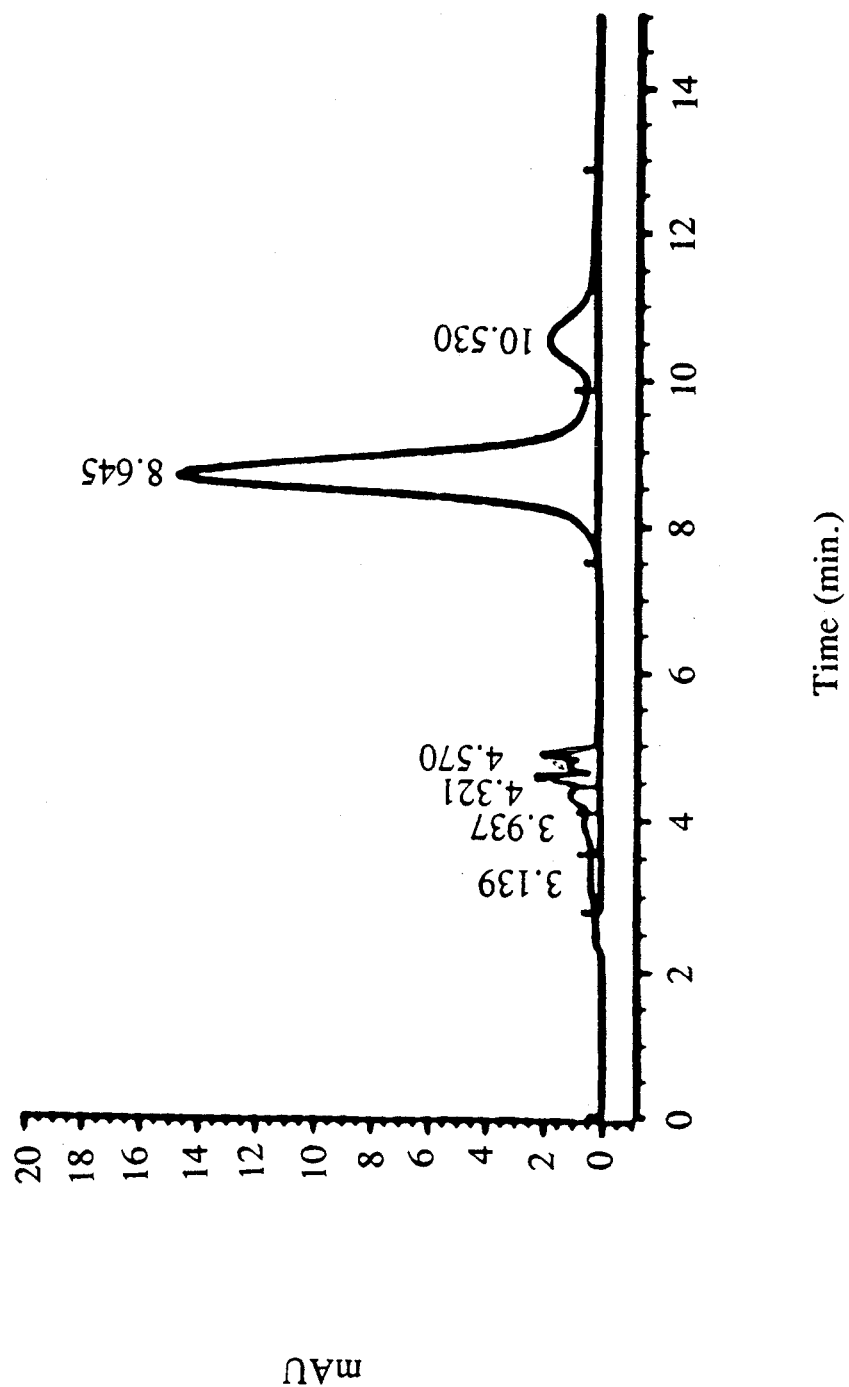
Figure 11C:
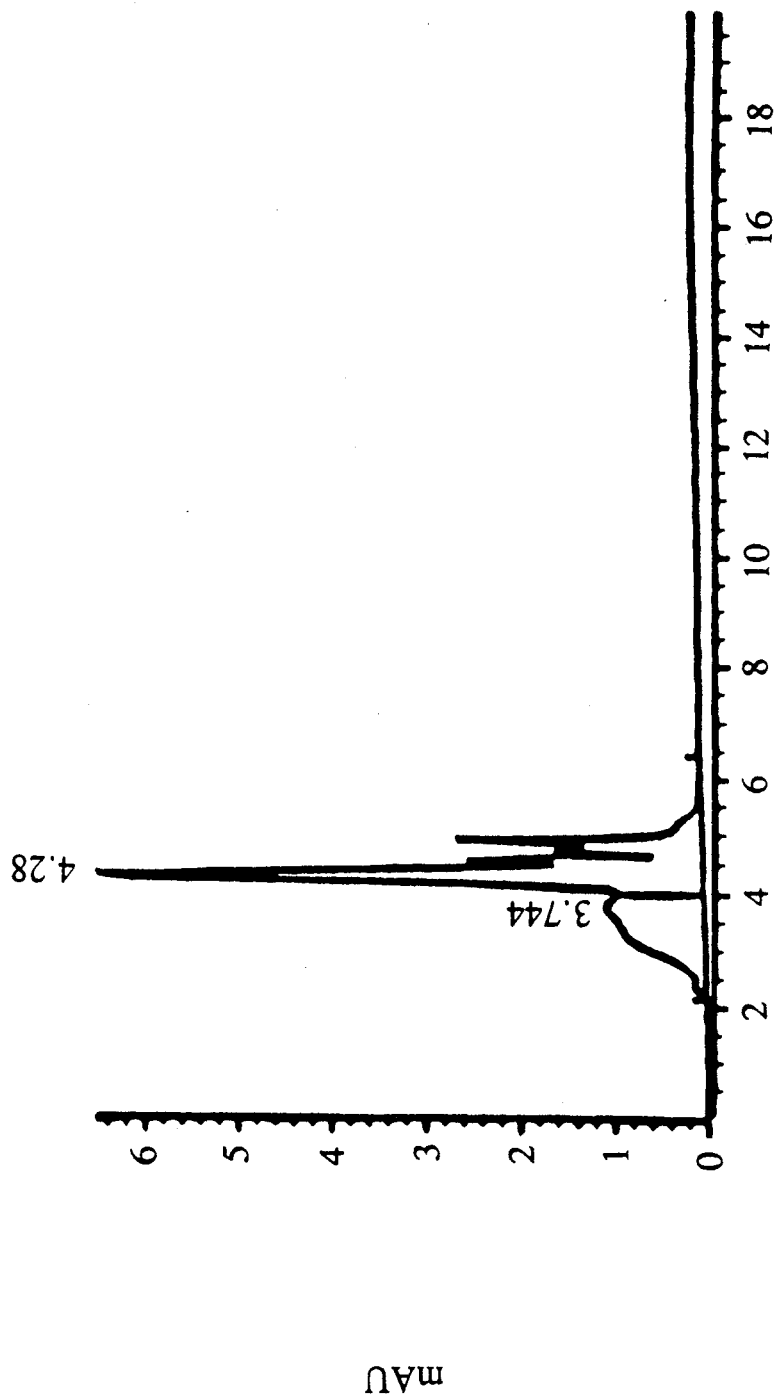

The remaining samples in columns 2, 3 and 4 were re-extracted with the same mixture (8.8 mole % toluene in $CO_2$), and at the same temperature (110° C.) as in the previous experiment, but at a higher pressure (7,000 psi), imparting a SCF solvent density of about 0.82 g/cc. Samples 2 and 4 were extracted in batch mode, while sample 3 was extracted continuously at a SCF flow rate of 2.4 ml/min. Total run time was 42 minutes. FIGS. 11a, 11b and 11c and Table 2 show the chromatograms of the three SFE samples and other fullerene recovery results from this run respectively.

TABLE 2

| Extraction of $C_{60}$ and $C_{70}$ from a Carbon Soot at Supercritical Conditions (7,000 psig. 110° C.). | | | | | | |
|---|---|---|---|---|---|---|
| Sample or Column Number | $C_{60}$ in Sample (mg) | $C_{70}$ in Sample (mg) | Recovery of $C_{60}$ (mg) | Recovery of $C_{70}$ (mg) | Recovery of $C_{60}$ (%) | Recovery of $C_{70}$ (%) |
| 2 | 2.62 | 0.35 | 0.0136 | N.D. | 3.9 | N.D. |
| 3 | 2.57 | 0.35 | 1.2600 | 0.2120 | ~49.0 | 60.4 |
| 4 | 0 | 0 | N.D. | N.D. | N.D. | N.D. |

It is noted that the amount of $C_{60}$ extracted from sample 3 was about 20-fold the amount extracted from the fresh carbon soot sample in the 5,000 psi run. Thus, as in the previous runs with the 14% toluene/$CO_2$ mixture, a marked increase in recovery occurs in the range 5,000-7,000 psig where the density of the solvent mixture is greater than 0.8 g/cc. Recoveries of both $C_{60}$ and $C_{70}$ from sample 3 are now quantitative, indicating that the density of the SCF mixture is above the threshold solubility densities of the solutes, and the phase behavior is now favorable for transfer of the fullerenes into the solvent phase. Hence, this lower concentration of toluene appears to have a favorable effect on the solubility of the fullerenes in the binary solvent mixture.

Single pass batch extracts from sample 2 contained essentially no $C_{70}$ and contained little $C_{60}$. Extract from sample 4 contained no contaminant, indicating once again that no cross-contamination between sample took place.

EXAMPLE 5: OPTIMIZATION OF CHROMATOGRAPHIC SEPARATIONS

The effects of PSDVB pore size and mobile phase on the chromatographic separation of fullerenes ($C_{60}$ and $C_{70}$) were studied to establish an optimized set of separation conditions.

1. Effect of column packing pore size

Three Envirosep-ABC columns, 300×7.8 mm, containing 10 μm average O.D. resin beads having average pore sizes of 50, 100, and 500 Å, were used under identical chromatographic conditions (see footnote in Table 3) to study the effect of column packing pore size on resolution (R), selectivity (α), capacity factor (k'), and column efficiency (peak height/peak area (HEIGHT/AREA), or number of theoretical plates (N)). As displayed in Table 3, selectivity (α) for $C_{60}$ and $C_{70}$ decreased with increasing pore size. Selectivity is only affected by the chemistry of the column packing, and not by the surface area of the packing (i.e., other chromatography parameter such as mobile phase, column temperature, and flow-rate were held constant). The amount of divinylbenzene (the % cross-linkage of polystyrene) is the only difference in these three packings. Thus, the amount of divinylbenzene in the column packing affects the selectivity of $C_{60}$ and $C_{70}$.

The capacity factor (k') of $C_{60}$ and $C_{70}$ is inversely proportional to the pore size of the packing. The higher k' is probably due to the larger surface area of the smaller pore size packing. The separation of $C_{60}$ and $C_{70}$ on the PSDVB column is affected by the π—π electron interaction of $C_{60}$ and $C_{70}$ with the porous polymer. The separation is not the result of size exclusion. The 100 Å pore size column packing displayed the best results for resolution (R) and speed (k').

TABLE 3

Effect of resin pore size on the separation of $C_{60}$ and $C_{70}$.

| Pore Size | | | K' | | HEIGHT/AREA | |
|---|---|---|---|---|---|---|
| (Å) | R | α | $C_{60}$ | $C_{70}$ | $C_{60}$ | $C_{70}$ |
| 50 | 1.84 | 1.34 | 3.58 | 4.79 | 0.024 | 0.018 |
| 100 | 2.19 | 1.29 | 2.80 | 3.61 | 0.034 | 0.025 |
| 500 | 2.04 | 1.25 | 2.41 | 3.01 | 0.043 | 0.028 |

$N = 5.545 \times (t_R \times 0.939)^2 \times (HEIGHT/AREA)^2$.
$\alpha = (T_{RC70} - T_0)/(T_{RC60} - T_0)$.
$T_0$ = Retention time at void volume.
$K' = (T_R - T_0)/T_0$
$R = (T_{RC70} - T_{RC60}) \times 2.35 / (W(50)_{C70} - W(50)_{C60})/2$
W(50) = Peak width at half height.
Columns: Envirosep-ABC 300 × 7.8 mm.
Eluent: 100% Methylene Chloride.
Flow Rate: 2.0 ml/min.
Column Temperature: 40° C.

2. Effect of Source of Column Packings and Column Dimension

Separation of $C_{60}$ and $C_{70}$ on nine columns with different rigid polystyrene divinylbenzene packings and column dimensions were studied. These columns were:

Envirosep-ABC columns:
    300 × 7.8 mm, 10 μm, 50 Å;
    300 × 7.8 mm, 10 μm, 100 Å;
    300 × 7.8 mm, 10 μm, 500 Å;
    300 × 15.0 mm, 10 μm, 50 Å;
    300 × 22.5 mm, 10 μm, 50 Å;
    300 × 22.5 mm, 10 μm, 100 Å;
    300 × 22.5 mm, 10 μm, 500 Å.
Waters Associates (Milford, MA) column:
    Ultrastyragel, 300 × 19.0 mm, 500 Å.
Hamilton Co. (Reno, Nev.) column:
    PRP-1, 100 × 10.0 mm, 5 μm.

Resolution (R), selectivity (α), capacity (k'), and column efficiency (HT/AR, N) were measured for each column using a solution of $C_{60}$ and $C_{70}$ dissolved in methylene chloride and are displayed in Table 4. Note that the selectivity (α) and capacity (k') are independent of column dimensions but dependent on the source of packings, and pore size. Column efficiency is inversely proportional to the column diameter.

The comparison of Envirosep-ABC (phenogel), Ultrastyragel, and PRP-1 gel columns provided some revealing results. The 500 Å Ultrastyragel and 500 Å Phenogel columns gave identical α value. This indicates that the molecular interactions of $C_{60}$ and $C_{70}$ with the two PSDVB layers are identical, i.e., there is no difference in the chemistry of these two PSDVB columns. The PRP-1 column is designed for reversed-phase mode separation. It has a very thin PSDVB layer (thus, a low surface area and smaller amount of PSDVB). This column has a very low retention of $C_{60}$ and $C_{70}$ (ca. k' ≈ 0). The large difference in capacity factor (k') observed with these three columns is in direct proportion to the surface area (i.e. thickness and pore size) of the PSDVB layer. The Ultrastyrgel column has a thicker PSDVB layer and Hamilton's PRP-1 packing has the thinnest PSDVB layer.

TABLE 4

Effect of rigid polystyrene divinylbenzene gel packings on separation of $C_{60}$ and $C_{70}$ fullerenes.

| Column | R | α | K' | | HEIGHT/AREA | |
|---|---|---|---|---|---|---|
| | | | $C_{60}$ | $C_{70}$ | $C_{60}$ | $C_{70}$ |
| Envirosep-ABC | | | | | | |
| 300 × 7.8 mm | | | | | | |
| 50 Å | 1.84 | 1.34 | 3.58 | 4.79 | 0.024 | 0.018 |
| 100 Å | 2.19 | 1.29 | 2.80 | 3.61 | 0.034 | 0.025 |
| 500 Å | 2.04 | 1.25 | 2.41 | 3.01 | 0.043 | 0.028 |
| 300 × 15.0 mm | | | | | | |
| 50 Å | 1.88 | 1.34 | 3.64 | 4.85 | 0.021 | 0.015 |
| 300 × 22.5 mm | | | | | | |
| 50 Å | | | | | | |
| 100 Å | 2.59 | 1.29 | 2.84 | 3.67 | 0.014 | 0.010 |
| 500 Å | 2.27 | 1.25 | 2.37 | 2.97 | 0.015 | 0.009 |
| Ultrastyragel | | | | | | |
| 300 × 19.0 mm | 2.19 | 1.29 | 2.80 | 3.61 | 0.034 | 0.025 |
| 500 Å | | | | | | |
| PRP-1 | No | Low | Low | | $C_{70}$ appears | |
| 100 × 10.0 mm | Sepa. | | | | as shoulder | |

Eluent and flow rate: Methylene chloride at 5 ml/min. for Envirosep-ABC and Ultrastyragel columns and 1 ml/min. for PRP-1 column.
Column Temperature: Ambient

3. Solubility of $C_{60}$ and $C_{70}$ in Toluene/Methylene Chloride

The very low solubility of $C_{60}$ and $C_{70}$ in organic solvents limits the chromatographic effectiveness and preparative throughput. The reported solubility of $C_{60}$ in benzene at room temperature is 5.0 mg/ml. The solubilities of $C_{60}$ and $C_{70}$ were established for the binary solvent system of toluene and methylene chloride using mixtures varying in composition from 100% to 0% of each component. The results are presented in Table 5.

The maximum amount of sample injected and the highest yield of $C_{60}$ per run, was achieved by using toluene as sample solvent and a 50/50, v/v, mixture of toluene and methylene chloride as mobile phase.

TABLE 5

Solubility of $C_{60}$ and $C_{70}$ fullerenes in Methylene Chloride/Toluene mixtures.

| SAMPLE NO. | % $CH_2Cl_2$ | % Toluene | mg/ml $C_{60}$ | mg/ml $C_{70}$ |
|---|---|---|---|---|
| 1 | 0.0 | 100 | 3.530 | 0.611 |
| 2 | 0.0 | 100 | 3.470 | 0.597 |
| 3 | 25.0 | 75 | 2.830 | 0.500 |
| 4 | 25.0 | 75 | 2.830 | 0.500 |
| 5 | 50.0 | 50 | 1.783 | 0.328 |
| 6 | 50.0 | 50 | 1.797 | 0.330 |
| 7 | 75.0 | 25 | 0.895 | 0.184 |
| 8 | 75.0 | 25 | 0.896 | 0.184 |
| 9 | 100.0 | 0 | 0.556 | 0.106 |
| 10 | 100.0 | 0 | 0.526 | 0.095 |

4. Effect of Injection Volume

Based on the data from the studies previously discussed, an Envirosep-ABC column packed with 100 Å, 10 micron particles, (300 ×22.5) was selected for the preparative separation of $C_{60}$ and $C_{70}$. The effects of injection volume, sample solvent (100% toluene vs 50% toluene/$CH_2Cl_2$, v/v), and mobile phase (toluene to methylene chloride ratio) on the separation were studied and the results are given in Table 6. These results revealed that separation decreased with increasing injection volume, and increasing ratio of toluene/methylene chloride in the sample solvent and mobile phase.

TABLE 6

Effect of injection volume, sample solvent, and mobile phase on separation of $C_{60}$ and $C_{70}$ fullerenes.

| Injection Volume (ml) | R | α | k' $C_{60}$ | k' $C_{70}$ | HEIGHT/AREA $C_{60}$ | HEIGHT/AREA $C_{70}$ |
|---|---|---|---|---|---|---|
| Elution Solvent: | | | | | | |
| 20% Tol. in $MeCl_2$ | | | | | | |
| 0.1 | 2.17 | 1.25 | 2.65 | 3.31 | 0.015 | 0.011 |
| 1.0 | 2.01 | 1.25 | 2.61 | 3.26 | 0.013 | 0.010 |
| 2.5 | 1.58 | 1.25 | 2.62 | 3.26 | 0.011 | 0.009 |
| 5.0 | 0.92 | 1.23 | 2.64 | 3.26 | 0.007 | 0.006 |
| 5.0* | 1.58 | 1.25 | 2.67 | 3.32 | 0.011 | 0.009 |
| Elution Solvent: | | | | | | |
| 50% Tol. in $MeCl_2$ | | | | | | |
| 1.0 | 1.59 | 1.20 | 2.35 | 2.83 | | |
| 2.5 | | | | | 0.014 | 0.011 |
| 5.0 | 0.86 | 1.19 | 2.39 | 2.84 | | |
| | | | | | 0.008 | 0.008 |

Column: Envirosep-ABC, 300 × 22.5 mm, 10 μm, 100 Å.
Sample: Saturated fullerene mixture in toluene diluted 500 times with toluene.
*Saturated fullerene mixture in toluene diluted 500 times with 50% toluene in methylene chloride. Column at ambient Temperature.

EXAMPLE 6: A QUANTITATIVE ANALYTICAL METHOD FOR $C_{60}$ AND $C_{70}$

Figure 12:
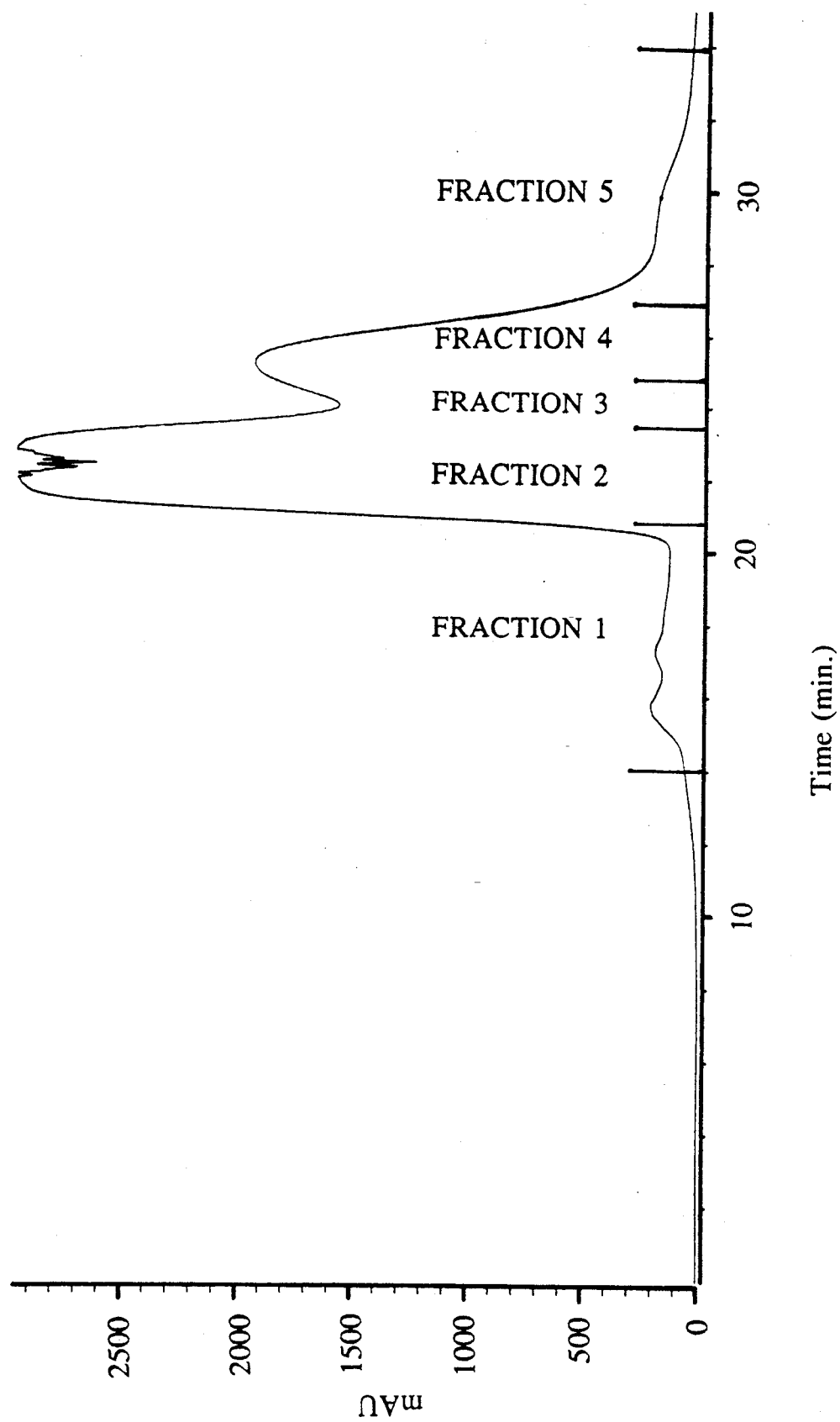
FIG. 12 illustrates the HPLC recovery of fullerene fractions in Example 6.

Two solutions were prepared from samples of MER mixtures of $C_{60}$ and $C_{70}$ for the preparative isolation of $C_{60}$ and $C_{70}$. Ten (10) preparative runs were made using the first sample solution and twenty (20) preparative runs were made using the second solution under the following chromatography conditions;

| Column: | Envirosep-ABC, 300 × 22.5 mm, 10 μm, 100 Å. |
|---|---|
| Flow-rate: | 5.0 ml/min. |
| Elution Solvent: | 50% methylene chloride in toluene, v/v, at ambient temperature. |
| Inject. Volume: | 4.5 ml. |
| Detector: | 330 nm, ± 40 nm |
| Sample Solut.: | 2.43 mg of ($C_{60}$ + $C_{70}$) / ml of toluene (MER sample). |
| Collect. Times: | (See FIG. 12) |
| Fraction 1: | 14.0-21.0 min. Toluene and unknown peaks. |
| Fraction 2: | 21.0-23.8 min. Mainly $C_{60}$. |
| Fraction 3: | 23.8-25.0 min. Mainly $C_{60}$ and $C_{70}$. |
| Fraction 4: | 25.0-26.8 min. Mainly $C_{70}$. |
| Fraction 5: | 26.8-34.0 min. Mainly $C_{82}$ and higher fullerenes. |

Data were obtained on the injection amount and injection volume effects on the purity and recovery of $C_{60}$ and $C_{70}$. Table 7 shows that the percentage of recovery of $C_{60}$ decreased slightly with increased injection volume and amount injected. The maximum fullerene capacity of the 300×22.5 mm column is estimated to be approximately 15 mg/4.5 ml.

Equivalent fractions from multiple runs were pooled and the purity and amount of fullerenes in these fractions were analyzed.

Pooled fraction 1: Contains a small amount of $C_{60}$ (ca 5%) and several unresolved unknown peaks that eluted before the $C_{60}$ peak. These peaks could be low molecular weight polynuclear aromatic hydrocarbons (having lower π-electron density), or partially formed fullerenes. The fraction was rechromatographed on a 500 Å column but no change in separation was noted.

Pooled fraction 2: Contains only $C_{60}$ (>95%)

Pooled fraction 3: Contains 42% $C_{60}$ and 58% $C_{70}$.

Pooled fraction 4: This fraction contains 11.4% $C_{60}$. A second isolation run was performed on this sample and the $C_{60}$ content was reduced to 3%.

Pooled fraction 5: Contains an enriched minor peak. Its UV spectrum and elution position indicate that it is probably $C_{82}$ molecule. About 2 mg of this unknown was obtained. Small quantities of $C_{60}$ and $C_{70}$ were still present in the fraction.

TABLE 7

Effect of sample size on semi-preparative separation of fullerenes $C_{60}$ and $C_{70}$.

| V. Injected in ml | Mass Injected (mg) $C_{60}$ $C_{70}$ | Amount (mg) and % Purity in Fraction 2 | | 3 | | 4 | | Total (mg and %) Recovered | % $C_{60}$ Recovrd |
|---|---|---|---|---|---|---|---|---|---|
| 2.5 | 4.65 | 3.62 | 96.3 | 0.156 | 26.2 | 0.251 | 25.1 | 4.03  86.7 | 90.0 |
|  | 1.41 | 0.14 | 3.70 | 0.439 | 73.7 | 0.747 | 74.9 | 1.33  84.3 |  |
| 3.5 | 6.58 | 4.95 | 95.9 | 0.172 | 26.5 | 0.348 | 22.3 | 5.47  83.1 | 90.5 |
|  | 1.98 | 0.21 | 4.10 | 0.468 | 72.2 | 1.210 | 77.7 | 1.89  95.4 |  |

TABLE 7-continued

Effect of sample size on semi-preparative separation of fullerenes $C_{60}$ and $C_{70}$.

| V. Injected in ml | Mass Injected (mg) $C_{60}$ $C_{70}$ | Amount (mg) and % Purity in Fraction 2 | | 3 | | 4 | | Total (mg and %) Recovered | | % $C_{60}$ Recovrd |
|---|---|---|---|---|---|---|---|---|---|---|
| 3.5 | 6.58 | 4.70 | 96.5 | 0.247 | 33.2 | 0.354 | 22.9 | 5.30 | 80.6 | 88.7 |
|  | 1.98 | 0.17 | 3.50 | 0.498 | 66.8 | 1.190 | 77.1 | 1.85 | 93.4 |  |
| 4.0 | 7.44 | 5.87 | 96.8 | 0.314 | 39.4 | 0.554 | 27.5 | 6.74 | 90.6 | 87.1 |
|  | 2.26 | 0.20 | 3.20 | 0.480 | 60.5 | 1.460 | 72.5 | 2.15 | 95.1 |  |
| 4.5 | 8.37 | No fractions collected | | | | | | 7.00 | 83.6 |  |
|  | 2.54 |  |  |  |  |  |  | 2.40 | 94.4 |  |

MER Sample Composition: $C_{60}$: 1.860 mg/ml of toluene
$C_{70}$: 0.565 mg/ml of toluene In conclusion, the above examples demonstrate the ability to adjust recovery or selectivity of solvents for fullerenes from a carbon soot using different solvent mixtures. Quantitative SFE recoveries are obtained when employing moderate amounts of a strong aromatic solvent modifier in $CO_2$ or other SCF. Selective SFE is obtained by employing moderate amounts of a non-aromatic modifier in $CO_2$. Higher recoveries can be achieved using other solvents mixtures, longer extraction times, and higher pressures and/or temperatures.

Fullerenes $C_{60}$ and $C_{70}$ are well separated with the Envirosep-ABC analytical columns. Semi-preparative isolation of C60 and C70 are obtained with the 300×22.5 mm column.

We claim:

1. A method for the separation and recovery of $C_{60}$ and $C_{70}$ fullerene components from a mixture comprising carbonaceous materials and fullerenes comprising the steps of:
   (a) extracting fullerenes from carbonaceous materials with a solvent entrained in a supercritical fluid to obtain a solvent containing extracted components,
   (b) introducing said solvent containing extracted components into a chromatographic column packed with a gel polymer or a macroreticular polymer material having a pore size of less than 500 Å and possessing aromaticity;
   (c) sequentially eluting $C_{60}$ and $C_{70}$ fullerenes from said column for recovery.

2. The method according to claim 1 wherein a first stage of the extraction of the fullerenes is accomplished by selective extraction of $C_{60}$ fullerene under supercritical conditions.

3. The method according to claim 1 wherein a residue containing unrecovered $C_{60}$ and $C_{70}$ fullerenes of the mixture remaining after fullerenes are extracted from the mixture in the extraction step is then reextracted at higher pressure or a higher temperature than in the first extraction step.

4. The method according to claim 1 wherein the extracting step is contacted at pressures between 1,000 and 50,000 psig.

5. The method according to claim 1 wherein the extracting step is conducted at temperatures between 31° and 400° C.

6. The method according to claim 1 wherein said extracted components are trapped on top of the column and subsequently eluted.

7. The method according to claim 1 wherein the chromatographic column is a low pressure column or a high performance column.

8. The method according to claim 1 wherein the supercritical fluid is carbon dioxide.

9. The method according to claim 1 wherein the gel polymer is a divinylbenzene crosslinked polystyrene.

10. The method according to claim 1 wherein the gel polymer is slurry packed in the chromatographic column.

11. The method according to claim 1 wherein said solvent entrained in a supercritical fluid comprises methylene chloride or toluene in carbon dioxide.

12. The method according to claim 1 wherein said supercritical fluid mixture possesses a density of at least 0.6 g/cc.

13. A method for the separation of components in a mixture containing fullerenes comprising:
   (a) providing a chromatographic column packed with a gel polymer or macroreticular polymer material having a pore size of less than 500 Å and possessing aromaticity, said polymer material being slurry packed in a solvent medium,
   (b) passing said mixture containing fullerenes through said packed column using a mobile phase comprising a supercritical fluid, or a mixture of a supercritical fluid and a modifier,
   (c) eluting the separated components.

14. The method according to claim 13 wherein the gel polymer material is a divinylbenzene crosslinked polystyrene gel material.

15. The method according to claim 13 wherein the gel polymer material has a pore size ranging between 10 to 500 Å.

16. The method according to claim 15 wherein the gel polymer material has a pore size less than 100 Å.

17. The method according to claim 13 wherein the gel polymer material is slurry packed in the column in a medium selected from the group consisting of methylene chloride, toluene, tetrahydrofuran, mixtures of methylene chloride with cyclohexane and mixtures of toluene with ethyl acetate.

18. The method according to claim 13 wherein the mobile phase is selected from the group consisting of hexane, heptane, isooctane, cyclopentane, methylene chloride, toluene, tetrahydrofuran, carbon disulfide, mixtures of methylene chloride with cyclohexane and mixtures of toluene with ethyl acetate.

19. The method according to claim 13 wherein the fullerene mixture containing fullerenes comprises $C_{60}$ and $C_{70}$ fullerenes.

20. The method according to claim 13 wherein the mixture containing fullerenes is an extract of carbon soot produced by liquid extraction, sublimation or supercritical fluid extraction.

21. The method according to claim 13 wherein $C_{60}$ and $C_{70}$ fullerenes are separated and recovered from other material present in the mixture containing fullerenes.

22. The method according to claim 13 wherein $C_{60}$ and $C_{70}$ fullerenes are separated from substituted $C_{60}$ and $C_{70}$ fullerenes.

23. The method according to claim 13 wherein the supercritical fluid comprises a mixture of carbon dioxide and toluene.

* * * * *